US010980501B2

(12) United States Patent
Tanabe et al.

(10) Patent No.: US 10,980,501 B2
(45) Date of Patent: Apr. 20, 2021

(54) X-RAY PHASE IMAGING APPARATUS

(71) Applicant: Shimadzu Corporation, Kyoto (JP)

(72) Inventors: Koichi Tanabe, Kyoto (JP); Kenji Kimura, Kyoto (JP); Toshinori Yoshimuta, Kyoto (JP); Taro Shirai, Kyoto (JP); Takahiro Doki, Kyoto (JP); Satoshi Sano, Kyoto (JP); Akira Horiba, Kyoto (JP); Naoki Morimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 417 days.

(21) Appl. No.: 15/958,188

(22) Filed: Apr. 20, 2018

(65) Prior Publication Data

US 2018/0306735 A1 Oct. 25, 2018

(30) Foreign Application Priority Data

Apr. 21, 2017 (JP) .............................. JP2017-084586

(51) Int. Cl.
*A61B 6/00* (2006.01)
*G01N 23/041* (2018.01)
(Continued)

(52) U.S. Cl.
CPC .............. *A61B 6/484* (2013.01); *A61B 6/405* (2013.01); *A61B 6/4035* (2013.01);
(Continued)

(58) Field of Classification Search
CPC .... A61B 6/00; A61B 6/06; A61B 6/08; A61B 6/40; A61B 6/4035; A61B 6/405;
(Continued)

(56) References Cited

U.S. PATENT DOCUMENTS

| 2010/0080436 A1 | 4/2010 | Ohara |
| 2013/0235973 A1* | 9/2013 | Murakoshi ............. A61B 6/502 378/37 |

(Continued)

FOREIGN PATENT DOCUMENTS

| DE | 102014213817 A1 * | 6/2015 | ............... A61B 6/44 |
| JP | 2012-016370 A | 1/2012 | |

(Continued)

OTHER PUBLICATIONS

English machine translation of DE 102014213817 (Leghissa) (Year: 2015).*

(Continued)

*Primary Examiner* — Anastasia Midkiff
(74) *Attorney, Agent, or Firm* — Muir Patent Law, PLLC

(57) ABSTRACT

The X-ray phase imaging apparatus includes a position switching mechanism for switching a relative position of one or more gratings between a retreated position which is an outside of a detection range on a detection surface of an image signal detector and a detection positon which is an inside of the detection range on the detection surface of the image signal detector and a focal diameter changing unit configured to change a focal diameter of the X-ray source in conjunction with switching of the relative position of the one or more gratings.

9 Claims, 18 Drawing Sheets

First Embodiment

Second Embodiment

(51) Int. Cl.
    *G21K 1/06* (2006.01)
    *G01N 23/20008* (2018.01)
    *G01N 23/20* (2018.01)
    *G01N 23/083* (2018.01)
    *G01T 1/164* (2006.01)
    *G21K 1/08* (2006.01)
    *G21K 1/10* (2006.01)

(52) U.S. Cl.
    CPC .......... *A61B 6/4291* (2013.01); *G01N 23/041* (2018.02); *G01N 23/20008* (2013.01); *G21K 1/06* (2013.01); *A61B 6/4452* (2013.01); *G01N 23/083* (2013.01); *G01N 23/20075* (2013.01); *G01N 2223/05* (2013.01); *G01N 2223/32* (2013.01); *G01N 2291/012* (2013.01); *G01T 1/1648* (2013.01); *G21K 1/08* (2013.01); *G21K 1/10* (2013.01); *G21K 2201/067* (2013.01); *G21K 2207/005* (2013.01)

(58) Field of Classification Search
    CPC .......... A61B 6/42; A61B 6/4291; A61B 6/44; A61B 6/4411; A61B 6/4429; A61B 6/4452; A61B 6/4478; A61B 6/48; A61B 6/484; A61B 6/54; A61B 6/547; A61B 6/548; A61B 6/587; A61B 6/588; A61B 2560/02; A61B 2560/0266; A61B 2560/04; A61B 2560/0406; A61B 2560/0443; A61B 2562/16; G01N 23/00; G01N 23/02; G01N 23/04; G01N 23/041; G01N 23/06; G01N 23/083; G01N 23/20; G01N 23/20008; G01N 23/20016; G01N 23/20025; G01N 23/20075; G01N 23/2055; G01N 2223/03; G01N 2223/04; G01N 2223/05; G01N 2223/056; G01N 2223/0566; G01N 2223/064; G01N 2223/30; G01N 2223/306; G01N 2223/308; G01N 2223/309; G01N 2223/313; G01N 2223/319; G01N 2223/32; G01N 2223/321; G01N 2223/40; G01N 2291/01; G01N 2291/012; G01N 2291/04; G01N 2291/045; G01N 2291/048; G01N 2291/102; H05G 1/00; H05G 1/02; G01T 1/244; G01T 1/29; G01T 1/2914; G01T 1/36; G21K 1/00; G21K 1/02; G21K 1/025; G21K 1/04; G21K 1/043; G21K 1/06; G21K 1/08; G21K 1/087; G21K 1/10; G21K 5/00; G21K 5/041; G21K 5/08; G21K 5/10; G21K 2201/00; G21K 2201/06; G21K 2201/067; G21K 2201/068; G21K 2207/00; G21K 2207/005

See application file for complete search history.

(56) References Cited

U.S. PATENT DOCUMENTS

2016/0231258 A1* 8/2016 Wen ...................... G01N 23/041
2019/0101496 A1* 4/2019 Doki ...................... A61B 6/484

FOREIGN PATENT DOCUMENTS

| JP | 2012-110395 A | 6/2012 |
|---|---|---|
| JP | 2012196557 A | 10/2012 |
| JP | 2014-030438 A | 2/2014 |

OTHER PUBLICATIONS

Notice of Reasons for Refusal dated Aug. 4, 2020 for corresponding Japanese Patent Application No. 2017-084586, submitted with a machine translation.

* cited by examiner

First Embodiment

First Embodiment

First Embodiment

Second Embodiment

Second Embodiment

Third Embodiment

Third Embodiment

Third Embodiment

Fourth Embodiment

Fourth Embodiment

First Modification of First Embodiment

Second Modification of First Embodiment

Fourth Modification of First Embodiment

X-RAY PHASE IMAGING APPARATUS

CROSS-REFERENCE TO RELATED APPLICATIONS

The priority application number JP2017-084586, entitled "X-ray phase imaging apparatus", filed on Apr. 21, 2017 and invented by Koichi Tanabe, Kenji Kimura, Toshinori Yoshimuta, Taro Shirai, Takahiro Doki, Satoshi Sano, Akira Horiba, and Naoki Morimoto, upon which this patent application is based is hereby incorporated by reference.

BACKGROUND OF THE INVENTION

Field of the Invention

The present invention relates to an X-ray phase imaging apparatus.

Background Technique

Conventionally, an X-ray phase imaging apparatus is known. Such an X-ray phase imaging apparatus is disclosed in, for example, Japanese Unexamined Patent Application Publication No. 2014-030438.

Japanese Unexamined Patent Application Publication No. 2014-030438 discloses an X-ray phase imaging apparatus having a phase image capturing mode for generating an X-ray phase contrast image of an object by fringe scanning and a normal image capturing mode for generating an image (absorption image) based on the intensity change of an X-ray due to an object.

This X-ray phase imaging apparatus is equipped with an X-ray source, a multi-slit, a first grating, a second grating, an image capturing unit (radiation image detection device) for detecting an X-ray from the X-ray source passed through an object to generate image data, a console for controlling the exposure operation of the X-ray source and the image capturing operation of the image capturing unit based on the operation of the operator, and a moving mechanism for moving the gratings. The console executes arithmetic processing of the image data acquired by the image capturing unit to generate an X-ray phase contrast image. The console is equipped with a control device. The X-ray source, the multi-slit, the first grating, the second grating, and the image capturing unit are arranged in this order in the optical axis direction of the X-ray.

This X-ray phase imaging apparatus is configured such that the control device drives the moving mechanism according to the input operation of the operator. This X-ray phase imaging apparatus is configured to switch between a phase image capturing mode and a normal image capturing mode by inserting the multi-slit, the first grating, and the second grating into the X-ray radiation field and retracing the multi-slit, the first grating, and the second grating from the X-ray radiation field via the moving mechanism.

In this case, in the case of capturing an image of an object which is small in thickness of one layer of a laminated carbon fiber reinforced plastic (CFRP) or a small (thin) tape-shaped carbon fiber bundle as an object, there is a disadvantage that a sufficient resolution cannot be obtained with a large focal diameter. Also, in the case of a small focal diameter, although sufficient resolution can be obtained, there is an inconvenience that an artifact (virtual image) is generated due to a multi-slit shadow when the focal diameter is smaller than the period of the multi-slit. Further, in the case of a small focal diameter, there is a disadvantage that there is a possibility that the dose necessary for obtaining an absorption image cannot be obtained because the dose of the irradiated X-ray becomes small. Note that the "artifact (virtual image)" means disturbance of an X-ray phase contrast image and/or deterioration of image quality of an X-ray phase contrast image due to shadows generated by partial interception of an X-ray by a grating.

In the X-ray phase imaging apparatus described in Japanese Unexamined Patent Application Publication No. 2014-030438, it is considered that an X-ray source having a large focal diameter is used since a multi-slit is provided in the X-ray source. Therefore, the X-ray phase imaging apparatus described in Japanese Unexamined Patent Application Publication No. 2014-030438 has a problem that sufficient resolution cannot be obtained. As a countermeasure, it is conceivable to reduce the focal diameter of the X-ray source of the X-ray phase imaging apparatus described in Japanese Unexamined Patent Application Publication No. 2014-030438. However, when the focal diameter of the X-ray source is reduced, there arises another problem that an artifact (virtual image) is generated by the multi-slit. Further, in cases where the X-ray source of the X-ray phase imaging apparatus described in Japanese Unexamined Patent Application Publication No. 2014-030438 is changed to an X-ray source having a small focal diameter, there arises another problem that the dose of the X-ray becomes insufficient when switching from the state of acquiring an X-ray phase contrast image with high resolution to a state of acquiring an absorption image.

The present invention was made to solve the aforementioned problems, and an object of the present invention is to provide an X-ray phase imaging apparatus capable of switching between acquisition of an X-ray phase contrast image and acquisition of an absorption image and also capable of acquiring an image with suitable resolution while suppressing occurrence of an artifact (virtual image) even when switching images to be acquired.

SUMMARY OF THE INVENTION

In order to achieve the aforementioned object, an X-ray phase imaging apparatus according to one aspect of the present invention includes an image signal generation system including an X-ray source and an image signal detector for detecting an image signal based on an X-ray irradiated from the X-ray source, one or more gratings arranged between the X-ray source and the image signal detector, a position switching mechanism configured to relatively move at least either the image signal generation system or the one or more gratings to switch a relative position of the one or more gratings between a retracted position which is an outside of a detection range on a detection surface of the image signal detector and a detection position which is an inside of the detection range on the detection surface of the image signal detector, and a focal diameter changing unit configured to change a focal diameter of the X-ray source in conjunction with switching of the relative position of the one or more gratings.

In the X-ray phase imaging apparatus according to one aspect of the present invention, as described above, the apparatus includes an image signal generation system including an X-ray source and an image signal detector, one or more gratings arranged between the X-ray source and the image signal detector, a position switching mechanism configured to relatively move at least either the image signal generation system or the one or more gratings to switch the relative position of the one or more gratings between the retracted position and the detection position, and a focal diameter changing unit for changing a focal diameter of the X-ray source in conjunction with switching of the relative position of the one or more gratings.

With this configuration, it is possible to change the focal diameter in conjunction with the movement of the grating arranged in the X-ray source. As a result, even in cases where the focal diameter of the X-ray source is changed to a focal diameter smaller than the pitch of the grating arranged in the X-ray source in order to acquire a high resolution X-ray phase contrast image, it is possible to arrange the grating arranged in the X-ray source in the retracted position. Therefore, it is possible to suppress the occurrence of an artifact (virtual image) due to the grating arranged in the X-ray source.

Also, by arranging the grating arranged in the X-ray source in the detection position and increasing the focal diameter of the X-ray source, a low resolution X-ray phase contrast image can be acquired. In addition, in the case of acquiring an absorption image, by changing the focal diameter in conjunction with the movement of the one or more gratings, a high resolution absorption image suitable for a size (thickness) and/or a material of an object can be acquired. Therefore, it is possible to switch between acquisition of an X-ray phase contrast image and acquisition of an absorption image, and even when an image to be acquired is switched, it is possible to acquire an image with suitable resolution while suppressing the occurrence of an artifact (virtual image).

In the X-ray phase imaging apparatus according to the aforementioned one aspect of the present invention, it is preferably configured such that the one or more gratings include two gratings. The two gratings include a self-image forming grating for forming a self-image by being irradiated by the X-ray from the X-ray source and an interference fringe forming grating for forming an interference fringe with the self-image of the self-image forming grating by being irradiated by the X-ray passed through the self-image forming grating. The position switching mechanism switches at least either the self-image forming grating or the interference fringe forming grating between the retracted position and the detection position.

In cases where the coherence of the X-ray irradiated from the X-ray source is high, it is not necessary to arrange a grating (multi-slit) for enhancing the X-ray coherence in the X-ray source, and an X-ray phase contrast image can be generated by the self-image forming grating and the interference fringe forming grating. With this configuration, since no multi-slit is arranged in the X-ray source, the focal diameter of the X-ray source can be freely changed. As a result, when generating an X-ray phase contrast image, it is possible to switch between low resolution and high resolution within the range capable of generating an interference fringe by the self-image forming grating and the interference fringe forming grating.

Since the period of the self-image formed by the self-image forming grating is smaller than the pixel pitch of a general-purpose detector, in cases where no interference fringe forming grating is arranged, the self-image of the self-mage forming grating is not detected by the image signal detector. That is, in cases where the interference fringe forming grating is arranged in the retracted position, the image to be acquired is an absorption image. Therefore, by switching the relative position of either the self-image forming grating or the interference fringe forming grating between the retracted position and the detection position, the acquisition of the X-ray phase contrast image and that of the absorption image can be easily switched. Further, by changing the focal diameter in conjunction with the movement of the one or more gratings, a resolution absorption image suitable for a size (thickness) of the object can be acquired.

In the X-ray phase imaging apparatus according to the aforementioned one aspect of the present invention, it is preferably configured such that the one or more gratings include three gratings, the three gratings including a coherence enhancing grating for enhancing coherence of the X-ray irradiated from the X-ray source, a self-image forming grating for forming a self-image by being irradiated by the X-ray passed through the coherence enhancing grating, and an interference fringe forming grating for forming an interference fringe with the self-image of the self-image forming grating by being irradiated by the X-ray passed through the self-image forming grating, and the position switching mechanism switches at least either the coherence enhancing grating or the interference fringe forming grating between the retracted position and the detection position.

With this configuration, even in cases where the focal diameter of the X-ray source is set to be smaller than the period of the coherence enhancing grating in order to acquire a high resolution X-ray phase contrast image, by arranging the coherence enhancing grating in the retracted position, the occurrence of an artifact due to the coherence enhancing grating can be suppressed. Also, in cases where the focal diameter of the X-ray source is increased, by arranging the coherence enhancing grating in the detection position, a low resolution X-ray phase contrast image can be obtained. By switching the interference fringe forming grating between the retracted position and the detection position, it is possible to easily switch between the acquisition of the X-ray phase contrast image and the acquisition of the absorption image.

In the X-ray phase imaging apparatus according to the aforementioned one aspect of the present invention, it is preferably configured such that the one or more gratings include one grating which is a self-image forming grating for generating a self-image by being irradiated by the X-ray from the X-ray source, and the position switching mechanism switches the self-image forming grating between the retracted position and the detection position.

Reducing the focal diameter of the X-ray source enhances the coherence of the irradiated X-ray. Also, in cases where the pixel period of the image signal detector is small, the self-image of the self-image forming grating can be detected without arranging the interference fringe forming grating. Therefore, by configuring the self-image forming grating so that the self-image forming grating can be switched between the retracted position and the detection position, the X-ray phase contrast image can be acquired by reducing the focal diameter of the X-ray source.

Further, when the focal diameter of the X-ray source is increased, the coherence of the irradiated X-ray is decreased. Therefore, the self-image of the self-image forming grating will not be formed. That is, by increasing the focal diameter of the X-ray source, an absorption image can be acquired.

Moreover, by increasing the focal diameter of the X-ray source in conjunction with the movement of the self-image forming grating to the retracted position, there occurs no attenuation of the X-ray in the self-image forming grating, which can suppress the occurrence of an artifact in the absorption image.

In the X-ray phase imaging apparatus according to the aforementioned one aspect of the present invention, it is preferably configured such that the one or more gratings include two gratings, the two gratings including a coherence enhancing grating for enhancing the coherence of the X-ray irradiated from the X-ray source and a self-image forming grating for forming the self-image by being irradiated by the X-ray passed through the coherence enhancing grating, and the position switching mechanism switches at least either the coherence enhancing grating or the self-image forming grating between the retracted position and the detection position.

With this configuration, by reducing the focal diameter of the X-ray source and arranging the coherence enhancing grating in the retracted position, a high resolution X-ray phase contrast image can be easily obtained. Also, by increasing the focal diameter of the X-ray source and arranging the coherence enhancing grating in the detection position, it becomes possible to increase the dose of the X-ray, which in turn can shorten the acquisition time of the X-ray phase contrast image.

In the X-ray phase imaging apparatus according to the aforementioned one aspect of the present invention, it is preferably configured such that a plurality of gratings is provided, and the position switching mechanism switches all of the plurality of gratings between the retracted position and the detection position. With this configuration, at the time of acquiring the absorption image, all of the gratings can be arranged outside the detection range on the detection surface of the image signal detector.

As a result, the occurrence of an artifact due to the one or more gratings arranged in the detection range on the detection surface of the image signal detector can be further suppressed. In addition, since no grating is arranged in the detection range on the detection surface of the image signal detector, it becomes possible to suppress the X-ray attenuation due to the gratings, which in turn can shorten the image capturing time.

In the X-ray phase imaging apparatus according to the aforementioned one aspect of the present invention, it is preferably configured such that the position switching mechanism moves at least either the image signal generation system or the one or more gratings in a horizontal direction orthogonal to an optical axis direction of the X-ray or a vertical direction to switch the relative position of the one or more gratings between the retracted position and the detection position.

With this configuration, by linearly moving the image signal generation system and the one or more gratings in the horizontal direction or in the vertical direction, it becomes possible to switch between the retracted position and the detection position. As a result, the configuration of the apparatus can be simplified.

In the X-ray phase imaging apparatus according to the aforementioned one aspect of the present invention, it is preferably configured such that it further includes a moving mechanism for changing a distance between the X-ray source and the image signal detector in conjunction with switching of the relative position of the one or more gratings.

With this configuration, at the time of acquiring the X-ray phase contrast image, even in cases where the dose becomes insufficient by reducing the focal diameter of the X-ray source, by decreasing the distance between the X-ray source and the image signal detector, the dose of the detected X-rays can be increased. In addition, at the time of acquiring a high resolution absorption image by reducing the focal diameter of the X-ray source, the magnification of the object can be increased by increasing the distance between the X-ray source and the image signal detector. As a result, the usability (user's convenience) can be improved.

In the X-ray phase imaging apparatus according to the aforementioned one aspect of the present invention, it is preferably configured to further include a rotation mechanism for relatively rotating an object and either the image signal generation system or the one or more gratings in a rotational direction about a central axis of a vertical direction orthogonal to an optical axis direction of the X-ray.

With this configuration, in the case of performing the tomographic imaging (CT imaging) requiring a dose of the X-ray, the image capturing can be performed by increasing the focal diameter of the X-ray source. Also, in the case of capturing an image of a small object, it is possible to perform the image capturing by reducing the focal diameter of the X-ray source. Therefore, as compared with the case in which CT image capturing and image capturing of a small object are performed by separate apparatuses, the work efficiency can be improved.

DESCRIPTION OF PREFERRED EMBODIMENTS

Hereinafter, embodiments of the present invention will be described with reference to the attached drawings.

First Embodiment

The configuration of an X-ray phase imaging apparatus 100 according to a first embodiment of the present invention will be described with reference to FIGS. 1 to 4.

Configuration of X-Ray Phase Imaging Apparatus

First, the configuration of the X-ray phase imaging apparatus 100 according to the first embodiment of the present invention will be described with reference to FIGS. 1 and 2.

Figure 1:
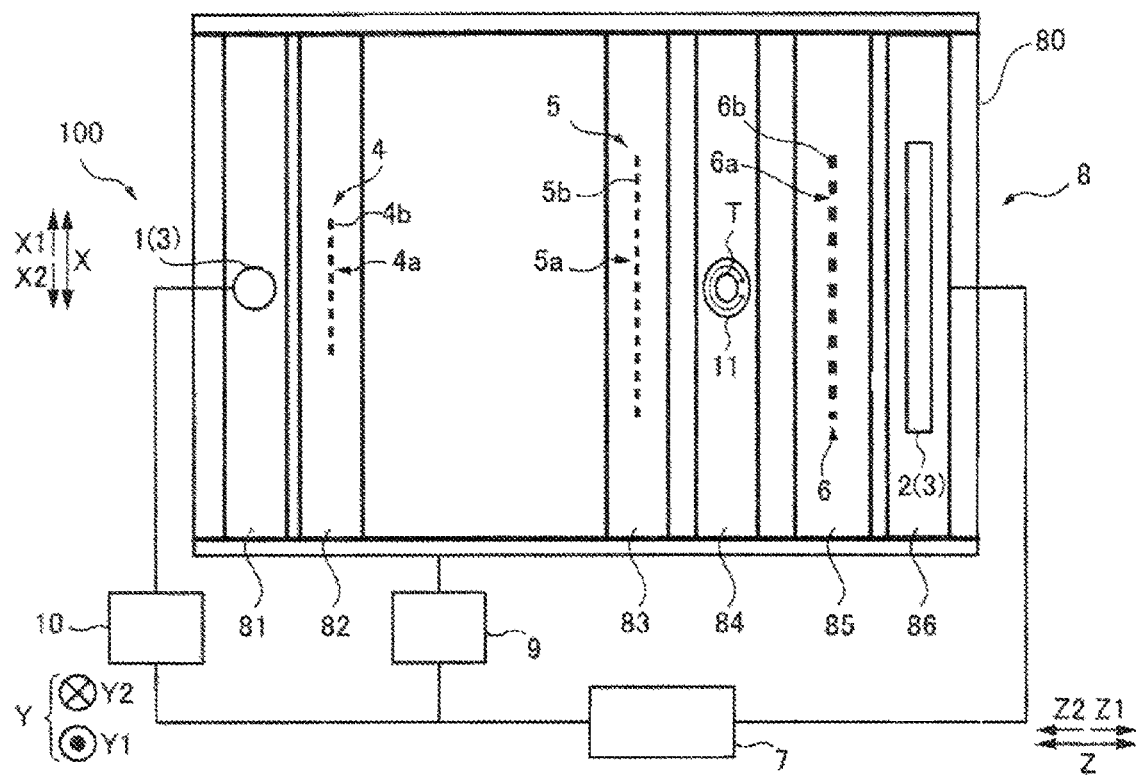
FIG. 1 is a plan view showing an overall structure of an X-ray phase imaging apparatus according to a first embodiment of the present invention.

As shown in FIG. 1, the X-ray phase imaging apparatus 100 is an apparatus for imaging the inside of an object T by utilizing the phase-contrast of the X-ray passed through the object T. Further, the X-ray phase imaging apparatus 100 is an apparatus for imaging the inside of the object T by utilizing the Talbot effect. Further, the X-ray phase imaging apparatus 100 is an apparatus for acquiring the absorption image of the object T based on the intensity change of the X-ray passed through the object T. For example, for non-destructive inspection applications, the X-ray phase imaging apparatus 100 can be used for capturing an image of the inside of the object T as a body. Further, for medical applications, for example, the X-ray phase imaging apparatus 100 can be used for capturing an image of the inside of the object T as a living body.

FIG. 1 is a plan view of the X-ray phase imaging apparatus 100 viewed from above. As shown in FIG. 1, the X-ray phase imaging apparatus 100 is equipped with an image signal generation system 3 including an X-ray source 1 and an image signal detector 2, a multi-slit 4, a phase grating 5, an absorption grating 6, a control device 7, a position switching mechanism 8, a position switching mechanism control unit 9, and a focal diameter changing unit 10.

In this specification, the direction from the X-ray source 1 to the multi-slit 4 is defined as a Z1-direction, and the opposite direction thereof is defined as a Z2-direction. Further, the left-right direction within the plane orthogonal to the Z-direction is defined as an X-direction. In the X-direction, a direction toward the upper side of the paper plane of FIG. 1 is defined as an X1-direction. Further, in the X-direction, a direction toward the lower side of the paper plane of FIG. 1 is defined as an X2-direction. Further, the vertical direction in a plane orthogonal to the Z-direction is defined as a Y-direction. In the Y-direction, a direction toward the back of the paper plane of FIG. 1 is defined as a Y2-direction. Also, in the Y-direction, a direction toward the front side of the paper plane of FIG. 1 is defined as a Y1-direction. The Z-direction is an example of the "optical axis direction of the X-ray" recited in claims. Also, the X-direction is an example of the "horizontal direction orthogonal to the optical axis direction of the X-ray" recited in claims. The Y-direction is an example of the "vertical direction orthogonal to the optical axis direction of the X-ray" recited in claims.

The multi-slit 4 is an example of the "coherence enhancing grating" recited in claims. The phase grating 5 is an example of the "self-image forming grating" recited in claims. The absorption grating 6 is an example of the "interference fringe forming grating" recited in claims.

The X-ray source 1 is configured to generate an X-ray by being applied by a high voltage and irradiate the generated the X-ray in the Z1-direction.

The multi-slit 4 is provided with a plurality of X-ray transmission portions 4a and X-ray absorption portions 4b arranged in a predetermined period (pitch) in the X-direction. Each of the X-ray transmission portions 4a and the X-ray absorption portions 4b is configured to extend in the Y-direction.

The multi-slit 4 is arranged between the X-ray source 1 and the phase grating 5 and is irradiated by an X-ray from the X-ray source 1. The multi-slit 4 is configured to make the X-ray that have passed through each of the X-ray transmission portions 4a as line light sources each corresponding to the position of each X-ray transmission portion 4a. With this, the multi-slit 4 can enhance the coherence of the X-ray irradiated from the X-ray source 1.

The phase grating 5 is provided with a plurality of slits 5a and X-ray phase change portions 5b arranged at a predetermined period (pitch) in the X-direction. The slits 5a and the X-ray phase change portions 5b are each formed so as to extend in the Y-direction.

The phase grating 5 is arranged between the multi-slit 4 and the absorption grating 6, and is irradiated by the X-ray passed through the multi-slit 4. The phase grating 5 is provided to form a self-image 50 (see FIG. 10A) by a Talbot effect. When an X ray with coherence passes through a grating in which slits are formed, an image of the grating (self-image 50) is formed at a position away from the grating by a predetermined distance (Talbot distance). This is called a Talbot effect.

The absorption grating 6 has a plurality of X-ray transmission portions 6a and X-ray absorption portions 6b arranged at a predetermined period (pitch) in the X-direction. The absorption grating 6 is arranged between the phase grating 5 and the image signal detector 2, and is irradiated by the X-ray passed through the phase grating 5. Further, the absorption grating 6 is arranged at a position away from the phase grating 5 by the Talbot distance. The absorption grating 6 interferes with the self-image 50 of the phase grating 5 to form a moire fringe (not shown) on the detection surface of the image signal detector 2.

The multi-slit 4, the phase grating 5, and the absorption grating 6 are gratings having different roles, and the X-ray transmission portion 4a, the slit 5a, and the X-ray transmission portion 6a respectively transmit the X-ray. The X-ray absorption portion 4b and the X-ray absorption portion 6b respectively play a role of shielding the X-ray, and the X-ray phase change portion 5b changes the phase of the X-ray by the difference of the refractive index with the slit 5a.

The detector 2 is configured to detect the X-ray, convert the detected X-ray into an electric signal, and read the converted electric signal as an image signal. The detector 2 is, for example, an FPD (Flat Panel Detector). The image signal detector 2 is composed of a plurality of conversion elements 2a (see FIG. 10A) and a plurality of pixel electrodes (not shown) arranged on the plurality of conversion elements 2a. The plurality of conversion elements 2a and pixel electrodes are arranged in an array in the X-direction and in the Y-direction at a predetermined period p3 (pixel pitch) (see FIG. 10B). Further, the image signal detector 2 is configured to output the acquired image signal to the control device 7.

Figure 2:
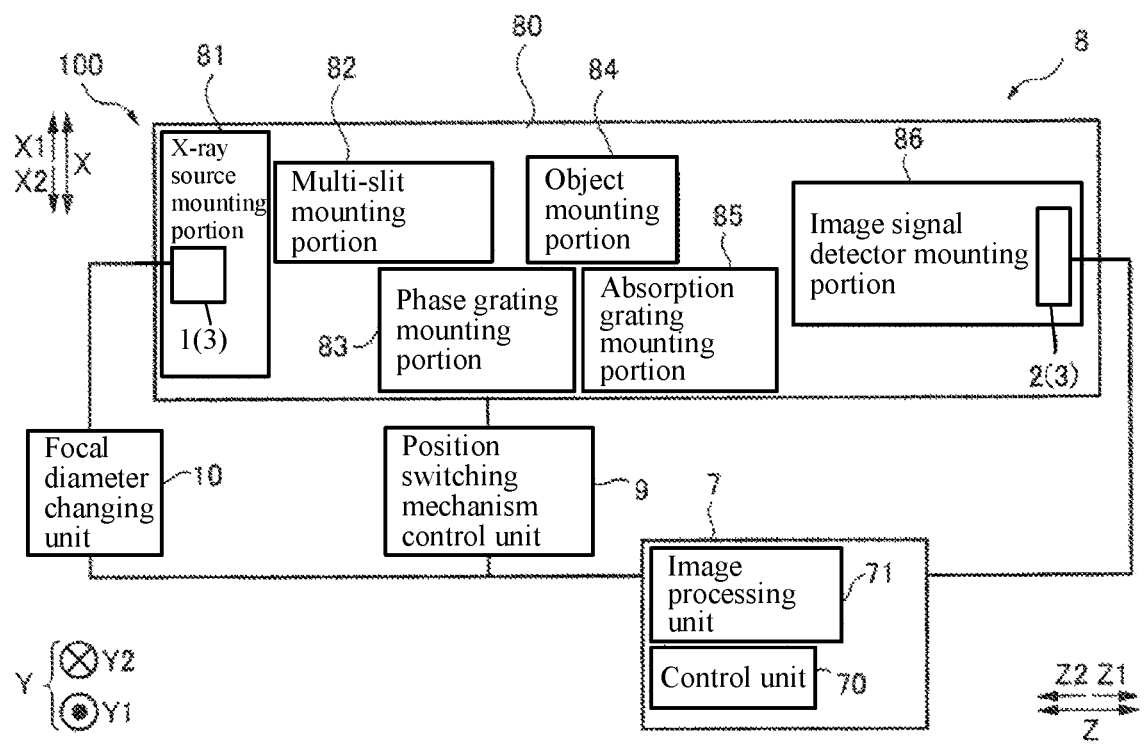
FIG. 2 is a block diagram showing an overall structure of the X-ray phase imaging apparatus according to the first embodiment of the present invention.

As shown in FIG. 2, the control device 7 includes a control unit 70 and an image processing unit 71. The control unit 70 is configured to output a signal for driving the position switching mechanism 8 to the position switching mechanism control unit 9. The control unit 70 is configured to output a signal for changing the focal diameter of the X-ray source 1 to the focal diameter changing unit 10. The image processing unit 71 is configured to image the image signal generated by the image signal generation system 3. The control device 7 is, for example, a PC (personal computer). Further, the control unit 70 includes, for example, a CPU (Central Processing Unit). The image processing unit 71 includes, for example, a GPU (Graphics Processing Unit).

The position switching mechanism control unit 9 is configured to control the position switching mechanism 8 based on the signal input from the control unit 70. The position switching mechanism control unit 9 includes, for example, a CPU (Central Processing Unit).

The position switching mechanism 8 is configured to switch the relative position of one or more gratings between a retracted position which is an outside of the detection range on the detection surface of the image signal detector 2 and the detection position which is an inside of the detection range on the detection surface of the image signal detector 2 by relatively moving at least either the image signal generation system 3 or the one or more gratings.

In this specification, the outside of the detection range on the detection surface of the image signal detector 2 denotes the outside of the range (the range where the region of interest of the object T is reflected in the image signal detector 2) where the X-ray passed through the region of interest of the object T is detected on the detection surface of the image signal detector 2. Therefore, even on the conversion element of the image signal detector 2, the location where the region of interest of the object T is not image-captured is the outside of the detection range.

Further, the inside of the detection range on the detection surface of the image signal detector 2 denotes the range (the range where the region of interest of the object T is reflected in the image signal detector 2) where the X-ray passed through the region of interest of the object T is detected on the detection surface of the image signal detector 2.

The focal diameter changing unit 10 is configured to change the focal diameter of the X-ray source 1 in conjunction with the switching of the relative position of one or more gratings based on the input from the control unit 70. Specifically, it is configured to change the focal diameter of the X-ray source 1 by changing the focus control of the X-ray source 1.

Switching Relative Position of Grating

Next, with reference to FIGS. 3 to 5, the configuration in which the X-ray phase imaging apparatus 100 according to the first embodiment switches the relative position of one or more gratings will be described.

Figure 3:
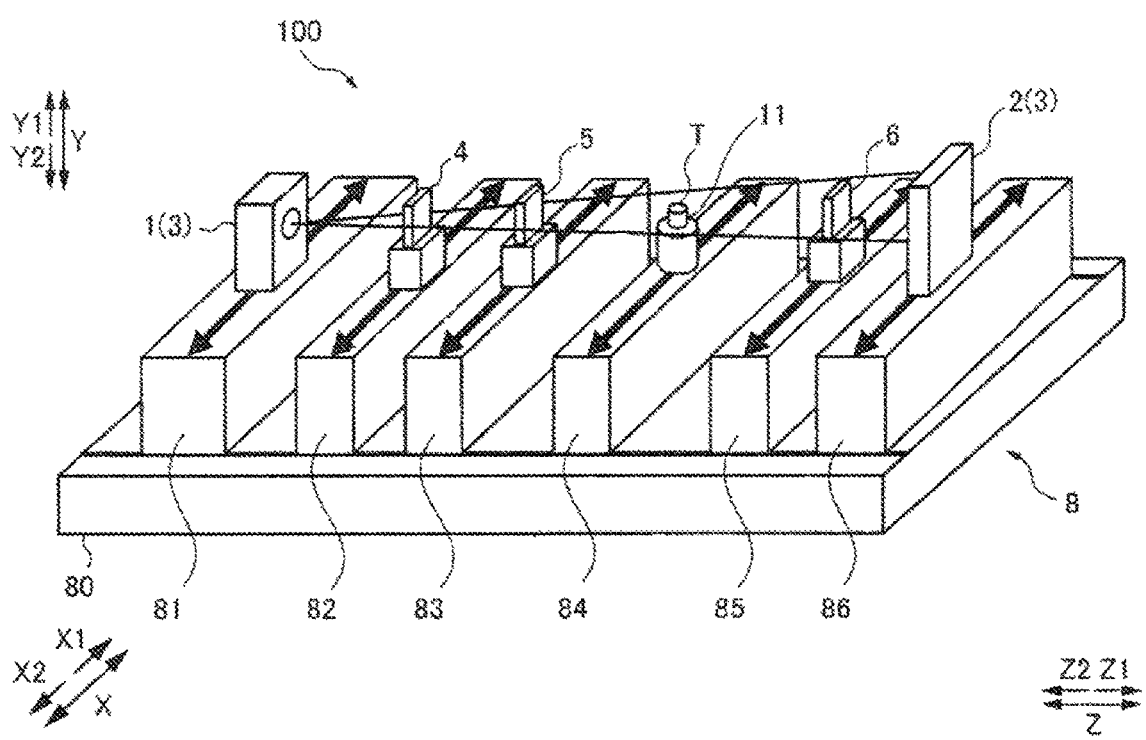
FIG. 3 is a perspective view for explaining detection positions of gratings of the X-ray phase imaging apparatus according to the first embodiment of the present invention.

As shown in FIG. 3, in the first embodiment, the multi-slit 4, the phase grating 5, and the absorption grating 6 are arranged in this order between the X-ray source 1 and the image signal detector 2. In the first embodiment, the object T is arranged on the object rotation mechanism 11 and is arranged between the phase grating 5 and the absorption grating 6. It should be noted that the object rotation mechanism 11 on which the object T is arranged is configured to be relatively rotatable in the rotational direction about the central axis of the Y-axis direction. Note that the object rotation mechanism 11 is an example of the "rotation mechanism" recited in claims.

In the first embodiment, the position switching mechanism 8 is composed of a Z-direction moving mechanism 80, an X-ray source mounting portion 81, a multi-slit mounting portion 82, a phase grating mounting portion 83, an object mounting portion 84, an absorption grating mounting portion 85, an image signal detector mounting portion 86.

The Z-direction moving mechanism 80 is configured to move the X-ray source mounting portion 81, the multi-slit mounting portion 82, the phase grating mounting portion 83, the object mounting portion 84, the absorption grating mounting portion 85, and the image signal detector mounting portion 86 in the Z1-direction and in the Z2-direction, respectively. It should be noted that the Z-direction moving mechanism 80 is an example of the "moving mechanism" recited in claims.

The X-ray source mounting portion 81 is configured to move the arranged X-ray source 1 in the X1-direction and in the X2-direction. In addition, the multi-slit mounting portion 82 is configured to move the mounted multi-slit 4 in the X1-direction and in the X2-direction.

Further, the phase grating mounting portion 83 is configured to move the mounted phase grating 5 in the X1-direction and in the X2-direction. The object mounting portion 84 is configured to move the mounted object T in the X1-direction and in the X2-direction.

Further, the absorption grating mounting portion 85 is configured to move the mounted absorption grating 6 in the X1-direction and in the X2-direction. The image signal detector mounting portion 86 is configured to move the mounted image signal detector 2 in the X1-direction and in the X2-direction. The Z-direction moving mechanism 80 includes, for example, a linear motion mechanism, such as, e.g., a ball screw and a linear motor. Further, the X-ray source mounting portion 81, the multi-slit mounting portion 82, the phase grating mounting portion 83, the object mounting portion 84, the absorption grating mounting portion 85, and the image signal detector mounting portion 86 each include a linear motion mechanism, such as, e.g., a ball screw and a linear motor.

In the first embodiment, at the time of acquiring a high resolution X-ray phase contrast image, the focal diameter of the X-ray source 1 is reduced by the focal diameter changing unit 10. At that time, as shown in FIG. 4, in order to suppress the occurrence of an artifact due to the multi-slit 4, the multi-slit 4 is moved to the retracted position which is the outside of the detection range on the detection surface of the image signal detector 2. That is, in the example shown in FIG. 4, the position switching mechanism 8 moves the multi-slit 4 in the X2-direction to arrange the multi-slit 4 in the retracted position.

Figure 4:
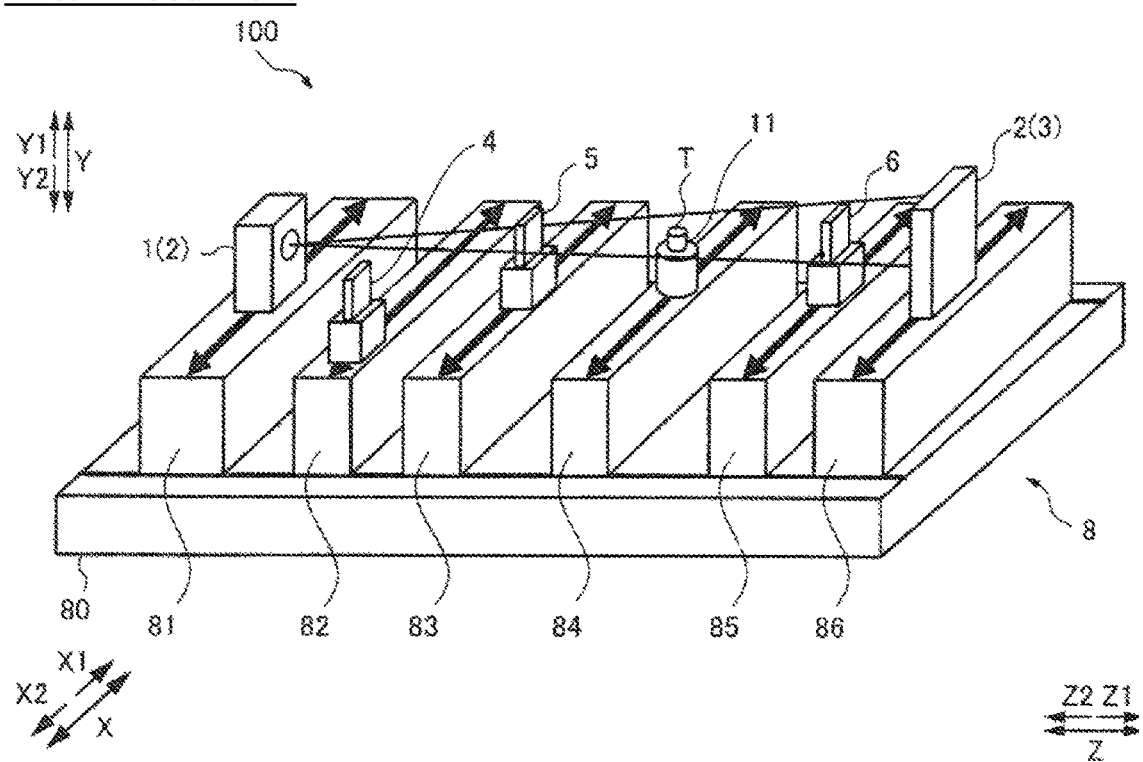
FIG. 4 is a perspective view for explaining a retracted position of a grating of the X-ray phase imaging apparatus according to the first embodiment of the present invention.
Figure 5:
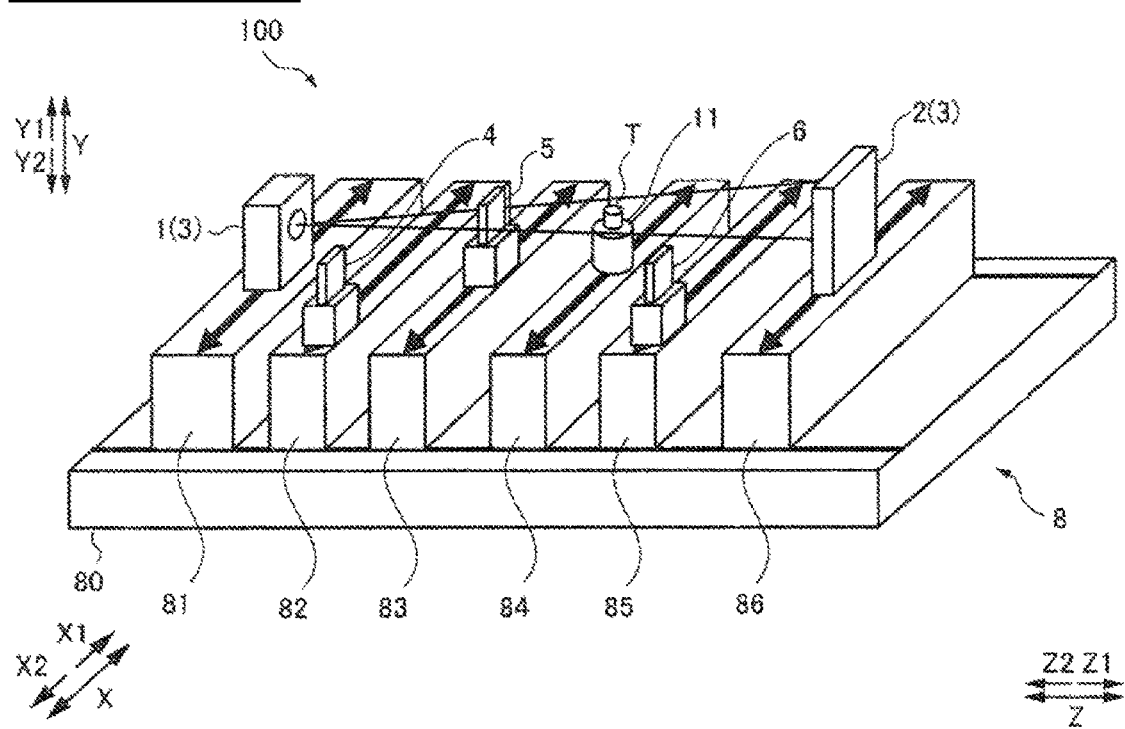
FIG. 5 is a perspective view for explaining the state after the movement of the X-ray phase imaging apparatus according to the first embodiment of the present invention in the optical axis direction of the X-ray.

In the example shown in FIG. 4, the example in which the multi-slit 4 is moved in the X2-direction is shown, but the absorption grating 6 may be moved in the X2-direction.

Further, both the multi-slit 4 and the absorption grating 6 may be moved in the X2-direction.

In the first embodiment, the dose of the X-ray decreases due to the reduced focal diameter of the X-ray source 1. For this reason, as shown in FIG. 5, the position switching mechanism 8 is configured to change the distance between the X-ray source 1 and the image signal detector 2 in conjunction with the switching of the relative position of one or more gratings. That is, the position switching mechanism 8 moves the multi-slit 4, the phase grating 5, the object T, the absorption grating 6, and the image signal detector 2 in the Z2-direction to thereby increase the dose of the X-ray to be detected by the image signal detector 2 (decrease the loss of the X-ray).

In the first embodiment, the following image can be acquired by changing the focal diameter of the X-ray source 1 in conjunction with the movement of one or more gratings. That is, by decreasing the focal diameter of the X-ray source 1, arranging the multi-slit 4 in the retracted position, and arranging the phase grating 5 in the detection position, it is possible to acquire a high resolution phase contrast image. Further, by increasing the focal diameter of the X-ray source 1 and arranging all of the gratings in detection positions, a low resolution phase contrast image can be acquired.

Further, by decreasing the focal diameter of the X-ray source 1 and arranging the phase grating 5 and/or the absorption grating 6 in the retracted position, a high resolution absorption image can be acquired. Further, by increasing the focal diameter of the X-ray source 1 and arranging the phase grating 5 and/or the absorption grating 6 in the retracted position, a low resolution absorption image can be acquired.

Effect of First Embodiment

In the first embodiment, the following effects can be obtained.

In the first embodiment, as described above, the X-ray phase imaging apparatus 100 includes the image signal generation system 3 including the X-ray source 1 and the image signal detector 2 for detecting the image signal based on the X-ray irradiated from the X-ray source 1, one or more gratings arranged between the X-ray source 1 and the image signal detector 2, the position switching mechanism 8 for switching the relative position of the one or more gratings between the retreated position which is the outside of the detection range on the detection surface of the image signal detector 2 and the detection position which is the inside of the detection range on the detection surface of the image signal detector 2 by relatively moving at least either the image signal generation system 3 or the one or more gratings, and the focal diameter changing unit 10 for changing the focal diameter of the X-ray source 1 in conjunction with the switching of the relative position of one or more gratings.

With this, the focal diameter can be changed in conjunction with the movement of the multi-slit 4. As a result, in order to acquire a high resolution X-ray phase contrast image, even in cases where the focal diameter of the X-ray source 1 is changed to a focal diameter smaller than the pitch of the multi-slit 4, it becomes possible to arrange the multi-slit 4 in the retracted position. Thus, the occurrence of an artifact (virtual image) due to the multi-slit 4 can be suppressed.

By arranging the multi-slit 4 in the detection position and increasing the focal diameter of the X-ray source 1, a low resolution X-ray phase contrast image can be acquired.

Further, in the case of acquiring an absorption image, by changing the focal diameter in conjunction with the movement of one or more gratings, an absorption image having resolution suitable for the size (thickness) or the material of the object T can be acquired. Therefore, it is possible to switch between acquisition of an X-ray phase contrast image and acquisition of an absorption image, and even when an image to be acquired is switched, it is possible to acquire an image with suitable resolution while suppressing the occurrence of an artifact (virtual image).

Further, in the first embodiment, as described above, it is configured such that the one or more gratings include three gratings, i.e., a multi-slit 4 for enhancing the coherence of the X-ray irradiated from the X-ray source 1, a phase grating 5 for forming a self-image 50 by being irradiated by the X-ray passed through the multi-slit 4, and an absorption grating 6 for forming an interference fringe with the self-image 50 of the phase grating 5 by being irradiated by the X-ray passed through the phase grating 5, and the position switching mechanism 8 switches at least either the multi-slit 4 or the absorption grating 6 between the retracted position and the detection position.

With this, even in cases where the focal diameter of the X-ray source 1 is made smaller than the period of the multi-slit 4 in order to acquire a high resolution X-ray phase contrast image, by arranging the multi-slit 4 in the retracted position, the occurrence of an artifact due to the multi-slit 4 can be suppressed. Further, in cases where the focal diameter of the X-ray source 1 is increased, a low resolution X-ray phase contrast image can be acquired by arranging the multi-slit 4 in the detection position. By switching the multi-slit 4 between the retracted position and the detection position, it is possible to switch easily between acquisition of the X-ray phase contrast image and acquisition of the absorption image.

In the first embodiment, as described above, it is configured such that the relative positon of one or more gratings is switched between the retracted position and the detection position by moving the one or more of gratings in the X-direction. With this, by linearly moving the image signal generation system 3 and the one or more gratings in the X-direction, it becomes possible to switch the relative position of the one or more gratings between the retracted position and the detection position. Therefore, the apparatus configuration of the X-ray phase imaging apparatus 100 can be simplified.

Further, in the first embodiment, as described above, the X-ray phase imaging apparatus 100 is further provided with a Z-direction moving mechanism 80 for changing the distance between the X-ray source 1 and the image signal detector 2 in conjunction with the switching of the relative position of one or more gratings.

With this configuration, at the time of acquiring an X-ray phase contrast image, even in cases where the dose becomes insufficient by reducing the focal diameter of the X-ray source 1, by decreasing the distance between the X-ray source 1 and the image signal detector 2, the dose of the detected X-ray can be increased. Further, at the time of acquiring a high resolution absorption image by reducing the focal diameter of the X-ray source 1, the magnification of the object T can be increased by increasing the distance between the X-ray source 1 and the image signal detector 2. As a result, the usability (user's convenience) can be improved.

In addition, in the first embodiment, as described above, it is further provided with the object rotation mechanism 11 for relatively rotating the object T in the rotational direction about the central axis of the Y-direction. With this, in the case of performing tomography (CT image capturing) that requires a dose of the X-ray, the image capturing can be performed by increasing the focal diameter of the X-ray source 1. Further, in the case of capturing an image of a small object T, the image capturing can be performed by reducing the focal diameter of the X-ray source 1. Therefore, as compared with the case in which CT image capturing and image capturing of a small object T are performed by separate apparatuses, the work efficiency can be improved.

Second Embodiment

Next, the configuration of the X-ray phase imaging apparatus 200 according to a second embodiment of the present invention will be described with reference to FIGS. 6 and 7. In this second embodiment, unlike the first embodiment in which at least either the relative position of the multi-slit 4 or the absorption grating 6 among the multi-slit 4, the phase grating 5 and the absorption grating 6 is switched between the retracted position and the detection position, it is configured such that at least either the relative position of the phase grating 5 or the absorption grating 6 is switched between the retracted position and the detection position.

The same reference numerals are allotted to the same configurations as those of the first embodiment in the drawings, and the description thereof will be omitted.

Figure 6:
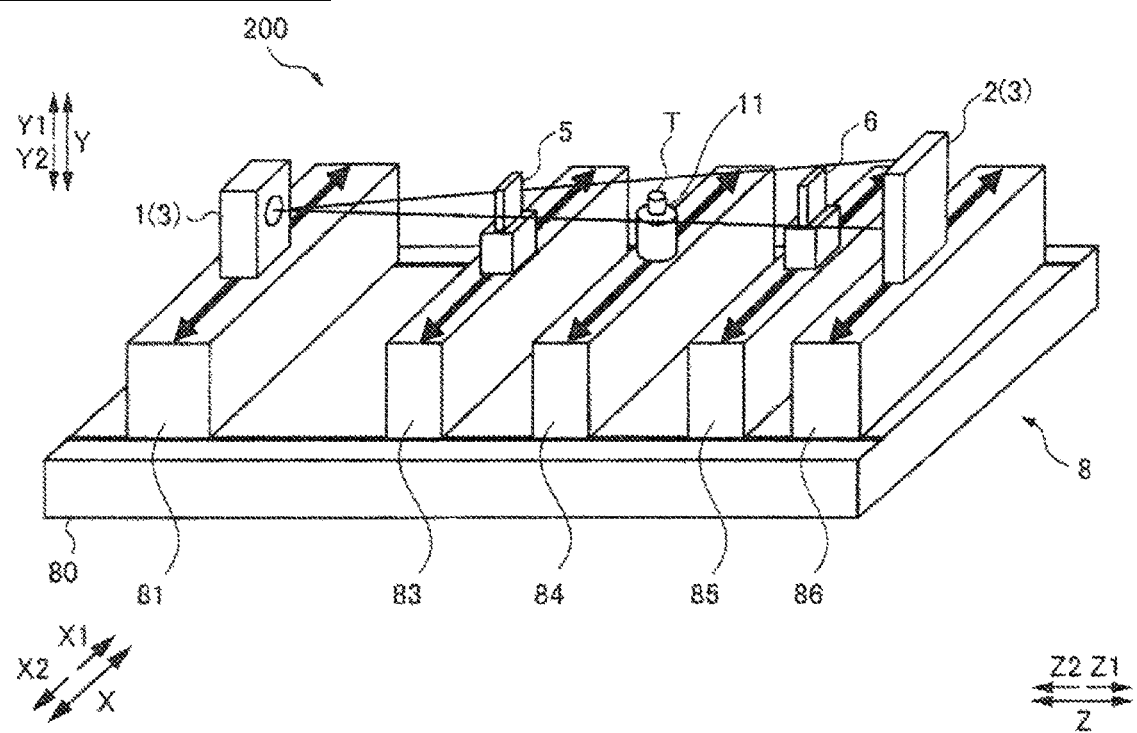
FIG. 6 is a perspective view for explaining detection positions of gratings of the X-ray phase imaging apparatus according to a second embodiment of the present invention.
Figure 7:
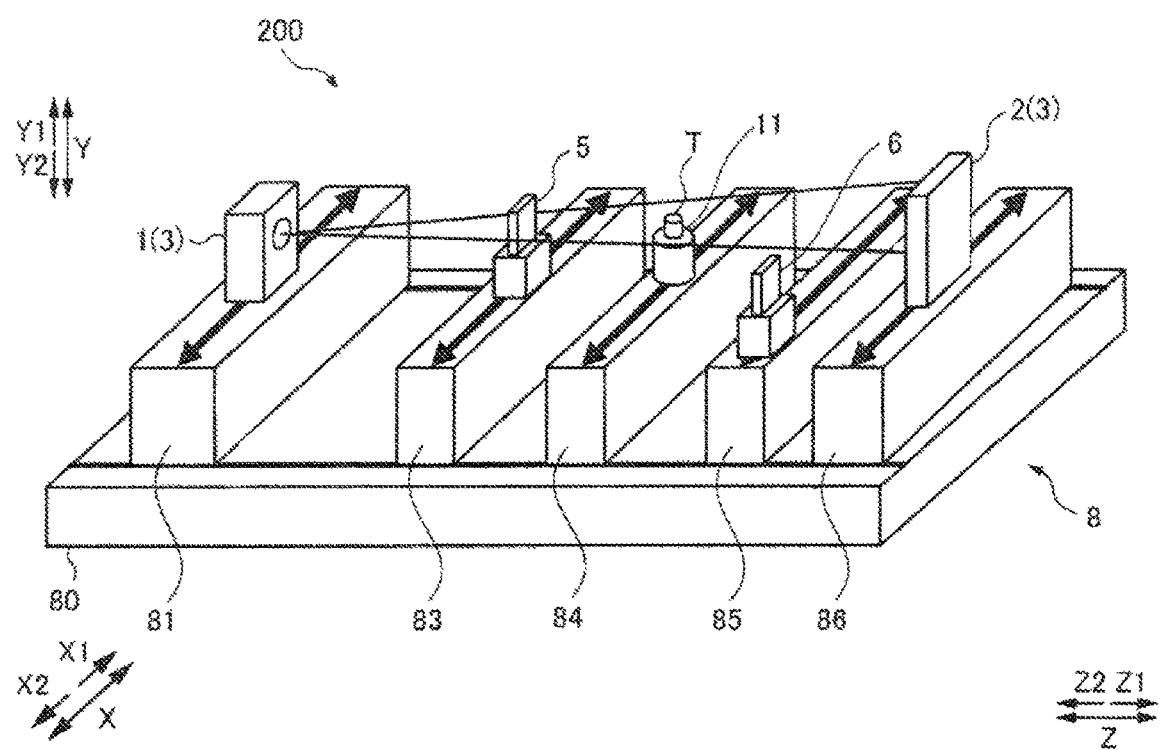
FIG. 7 is a perspective view for explaining a retracted position of a grating of the X-ray phase imaging apparatus according to the second embodiment of the present invention.

As shown in FIG. 6, in the X-ray phase imaging apparatus 200 according to the second embodiment, the one or more gratings include two gratings, i.e., a phase grating 5 for forming a self-image 50 by being irradiated by the X-ray from the X-ray source 1 and an absorption grating 6 for forming an interference fringe with the self-image 50 of the phase grating 5 by being irradiated by the X-ray passed through the phase grating 5. Further, the position switching mechanism 8 includes a Z-direction moving mechanism 80, an X-ray source mounting portion 81, a phase grating mounting portion 83, an object mounting portion 84, an absorption grating mounting portion 85, and an image signal detector mounting portion 86.

In the second embodiment, the position switching mechanism 8 is configured to switch at least either the phase grating 5 or the absorption grating 6 between the retracted position and the detection position. In the second embodiment, as shown in the example of FIG. 7, the position switching mechanism 8 is configured to move the absorption grating 6 in the X2-direction to switch between the retracted position and the detection position.

Here, in cases where the coherence of the X-ray irradiated from the X-ray source 1 is high, there is no need to arrange the multi-slit 4 in the X-ray source 1, and an X-ray phase contrast image can be generated by the phase grating 5 and the absorption grating 6. Therefore, in the second embodiment, in the case of acquiring an X-ray phase contrast image, the focal diameter of the X-ray source 1 is decreased in order to enhance the coherence of the X-ray. In the example shown in FIG. 7, the absorption grating 6 is moved in the X2-direction. However, the phase grating 5 may be moved in the X2-direction. Alternatively, both the phase grating 5 and the absorption grating 6 may be moved in the X2-direction.

In the second embodiment, the following image can be acquired by changing the focal diameter of the X-ray source 1 in conjunction with the movement of one or more gratings. That is, by decreasing the focal diameter of the X-ray source 1 and arranging all of the gratings in detection positions, a high resolution phase contrast image can be acquired.

Further, by decreasing the focal diameter of the X-ray source 1 and arranging the phase grating 5 and/or the absorption grating 6 in the retracted position, a high resolution absorption image can be acquired. By decreasing the focal diameter of the X-ray source 1 and arranging the phase grating 5 and/or the absorption grating 6 in the retracted position, a low resolution absorption image can be acquired.

Effects of Second Embodiment

In the second embodiment, the following effects can be obtained.

In the second embodiment, as described above, it is configured such that the one or more gratings include two gratings, i.e., the phase grating 5 for forming a self-image 50 by being irradiated by the X-ray from the X-ray source 1 and the absorption grating 6 for forming an interference fringe with the self-image 50 of the phase grating 5 by being irradiated by the X-ray passed through the phase grating 5, and the position switching mechanism 8 is configured to switch at least either the phase grating 5 or the absorption grating 6 between the retracted position and the detection position.

Here, in cases where the coherence of the X-ray irradiated from the X-ray source 1 is high, there is no need to arrange the multi-slit 4, and an X-ray phase contrast image can be generated by the phase grating 5 and the absorption grating 6. With this, since the multi-slit 4 is not arranged in the X-ray source 1, it becomes possible to freely change the focal diameter of the X-ray source 1. As a result, at the time of generating an X-ray phase contrast image, it is possible to switch between low resolution and high resolution within a range where an interference fringe can be formed by the phase grating 5 and the absorption grating 6.

The period p1 of the self-image 50 formed by the phase grating 5 is smaller than a pixel pitch p2 of a conversion element 2a of a general-purpose detector 2. Therefore, in cases where no absorption grating 6 is arranged, the self-image 50 of the phase grating 5 is not detected by the image signal detector 2. That is, when the absorption grating 6 is arranged in the retracted position, the image to be acquired becomes an absorption image. Therefore, by switching the relative position of either the phase grating 5 or the absorption grating 6 between the retracted position and the detection position, the acquisition of the X-ray phase contrast image and that of the absorption image can be easily switched. Further, by changing the focal diameter in conjunction with the movement of one or more gratings, it is possible to acquire an absorption image having a resolution according to the size (thickness) of the object T.

The other effects of the second embodiment are the same as those of the first embodiment.

Third Embodiment

Next, the configuration of an X-ray phase imaging apparatus 300 according to a third embodiment of the present invention will be described with reference to FIGS. 8 to 10. In this third embodiment, unlike the first embodiment in which the relative position of at least either the multi-slit 4 or the absorption grating 6 among the multi-slit 4, the phase grating 5, and the absorption grating 6 is configured to be switched between the retracted position and the detection position, the phase grating 5 is configured to be switched between the retracted position and the detection position.

The same reference numerals are allotted to the same configurations as those of the first embodiment in the drawings, and the description thereof will be omitted.

Figure 8:
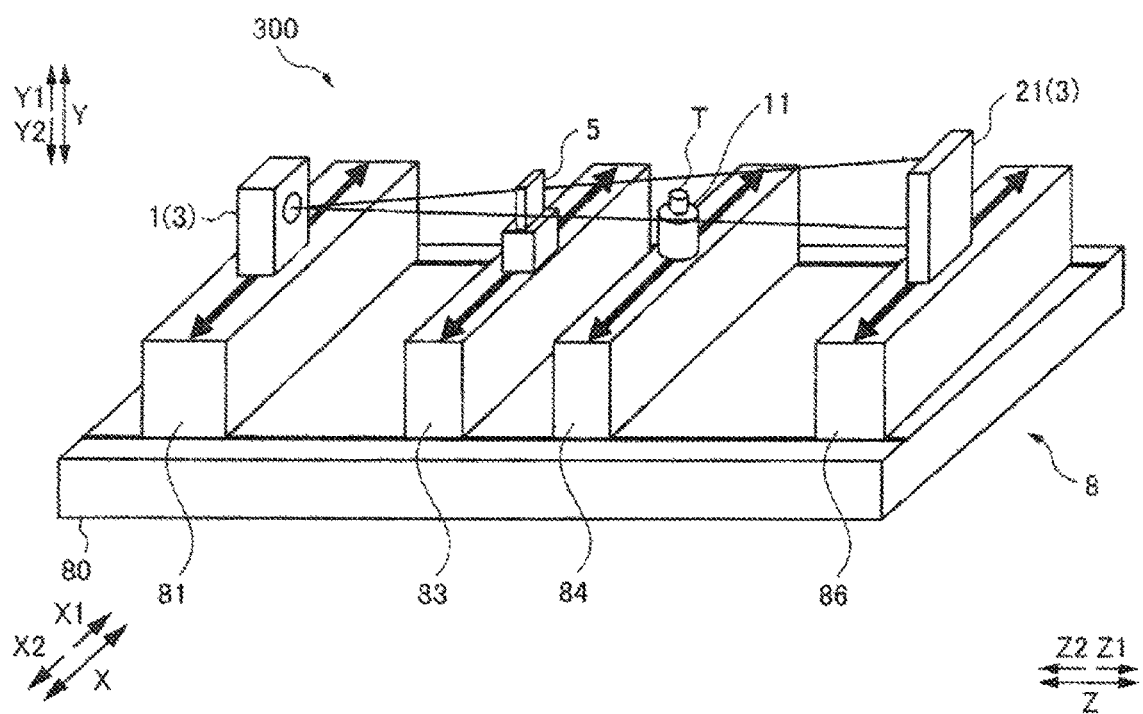
FIG. 8 is a perspective view for explaining a detection position of a grating of the X-ray phase imaging apparatus according to a third embodiment of the present invention.
Figure 9:
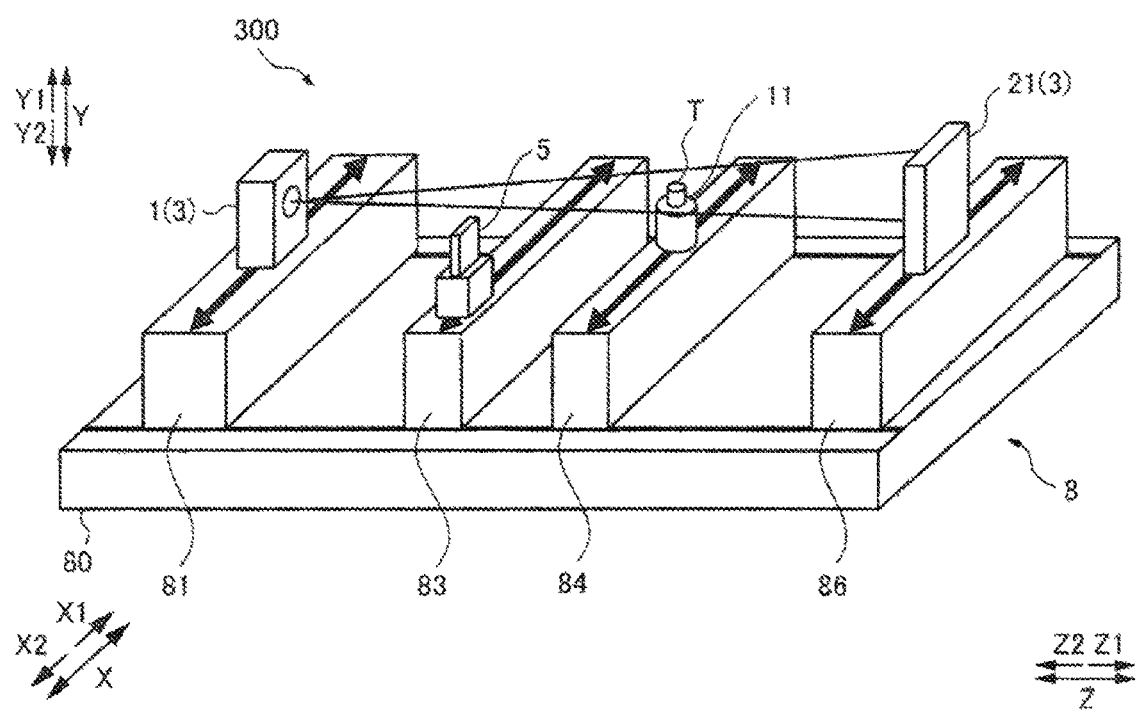
FIG. 9 is a perspective view for explaining a retracted position of a grating of the X-ray phase imaging apparatus according to the third embodiment of the present invention.

As shown in FIGS. 8 and 9, in the third embodiment, an image signal generation system 3 including an X-ray source 1 and an image signal detector 21, one grating which is a phase grating 5 for forming a self-image 50 by being irradiated by an X-ray from the X-ray source 1 as one or more gratings, and a position switching mechanism 8 are included. Further, the position switching mechanism 8 includes a Z-direction moving mechanism 80, an X-ray source mounting portion 81, a phase grating mounting portion 83, an object mounting portion 84, and an image signal detector mounting portion 86. The position switching mechanism 8 is configured to switch the phase grating 5 between the retracted position and the detection position. That is, the position switching mechanism 8 is configured to move the phase grating 5 in the X-direction to switch the relative position of the phase grating 5 between the retracted position and the detection position.

In the example shown in FIG. 9, the position switching mechanism 8 is configured to move the phase grating 5 in the X2-direction to switch between the retracted position and the detection position. In the example shown in FIG. 9, the position switching mechanism 8 is configured to move the phase grating 5 in the X2-direction, but the position switching mechanism 8 may be configured to move the phase grating 5 in the X1-direction.

Figure 10A:
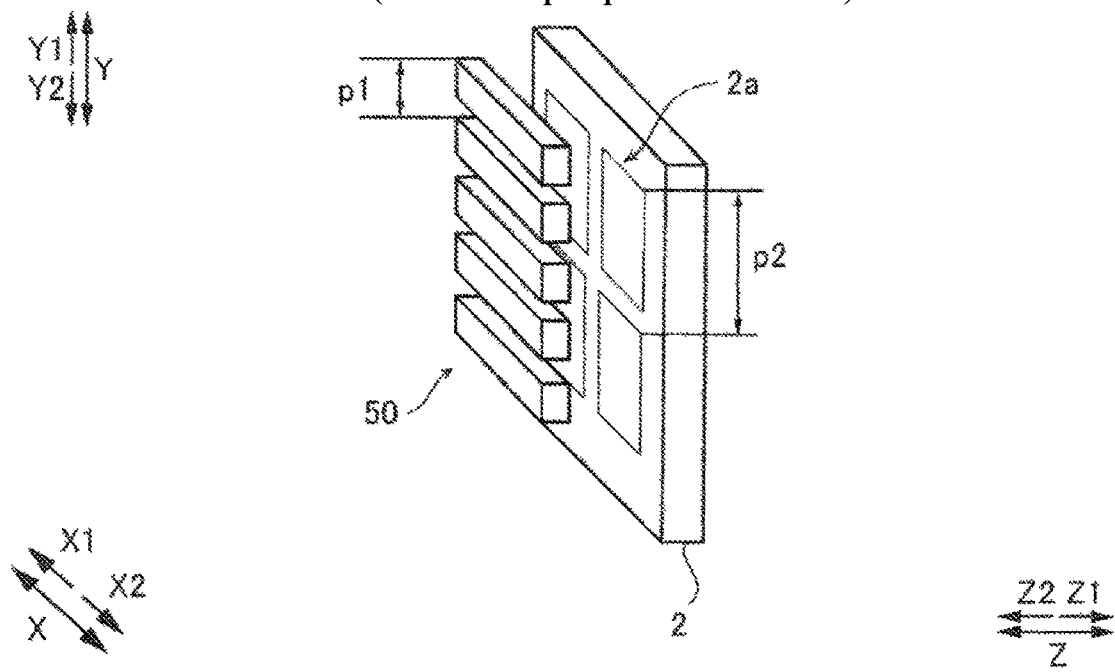
FIG. 10A is a diagram showing a magnitude of a pixel pitch of a conventional image signal detector.

Reducing the focal diameter of the X-ray source 1 enhances the coherence of the irradiated X-ray. In cases where the pixel period of the image signal detector 2 is small, it is possible to detect the self-image 50 of the phase grating 5 without arranging the absorption grating 6. Generally, as the image signal detector 2, a general-purpose detector 2 as shown in FIG. 10A is used.

Since the pixel pitch p2 of the conversion elements 2a of the detector 2 is larger than the period p1 of the self-image 50 of the phase grating 5, the self-image 50 of the phase grating 5 cannot be detected. However, by using the detector 21 shown in FIG. 10B, the self-image 50 of the phase grating 5 can be detected. That is, since the pixel pitch p3 of the conversion elements 21a of the detector 21 is smaller than the period p1 of the self-image 50 of the phase grating 5, the self-image 50 of the phase grating 5 can be detected.

Figure 10B:
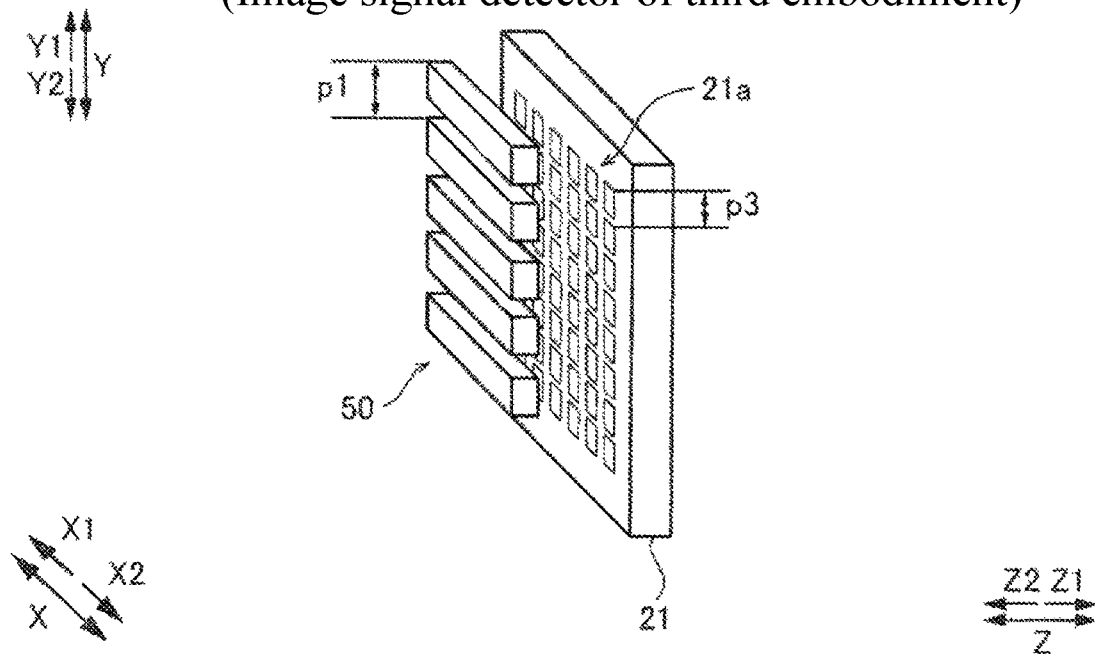
FIG. 10B is a diagram showing a magnitude of a pixel pitch of an image signal detector according to the third embodiment of the present invention.

In the third embodiment, as the image signal detector, as shown in FIG. 10B, a detector 21 whose pixel pitch is smaller than the period p1 of the self-image 50 of the phase grating 5 is used. With this, the image signal detector 21 can detect the self-image 50 of the phase grating 5.

In the third embodiment, the following image can be acquired by changing the focal diameter of the X-ray source 1 in conjunction with the movement of one or more gratings. That is, by decreasing the focal diameter of the X-ray source 1 and arranging the phase grating 5 in the detection position, a high resolution X-ray phase contrast image can be acquired.

Further, by decreasing the focal diameter of the X-ray source 1 and arranging the phase grating 5 in the retracted position, a high resolution absorption image can be obtained. Further, by increasing the focal diameter of the X-ray source 1 and arranging the phase grating 5 in the retracted position, a low resolution absorption image can be obtained.

In cases where the focal diameter of the X-ray source 1 is increased, the coherence of the X-ray is reduced. Therefore, even if the phase grating 5 is arranged at the detection position, the self-image 50 of the phase grating 5 is not formed, so the image to be acquired is an absorption image.

Effects of Third Embodiment

In the third embodiment, the following effects can be obtained.

In the third embodiment, as described above, it is configured such that the one or more gratings include one grating which is a phase grating 5 for forming a self-image 50 by being irradiated by the X-ray from the X-ray source 1 and that the position switching mechanism 8 switches the phase grating 5 between the retracted position and the detection position.

With this, by narrowing the focal diameter of the X-ray source 1, an X-ray phase contrast image can be acquired. Further, in cases where the focal diameter of the X-ray source 1 is increased, the coherence of the irradiated X-ray is decreased. For this reason, the self-image 50 of the phase grating 5 will not be formed. That is, by increasing the focal diameter of the X-ray source 1, an absorption image can be acquired.

Moreover, by increasing the focal diameter of the X-ray source 1 in conjunction with the movement of the phase grating 5 to the retracted position, there occurs no attenuation of the X-ray in the phase grating 5, which can suppress the occurrence of an artifact in the absorption image.

The other effects of the third embodiment are the same as those of the first embodiment.

Fourth Embodiment

Next, the configuration of the X-ray phase imaging apparatus 400 according to a fourth embodiment of the present invention will be described with reference to FIGS. 11 and 12. In this fourth embodiment, unlike the first embodiment in which at least either the relative position of the multi-slit 4 or the absorption grating 6 among the multi-slit 4, the phase grating 5, and the absorption grating 6 is switched between the retracted position and the detection position, it is configured to switch the relative position of at least either the multi-slit 4 or the phase grating 5 between the retracted position and the detection position.

The same reference numerals are allotted to the same configurations as those of the first embodiment in the drawings, and the description thereof will be omitted.

Figure 11:
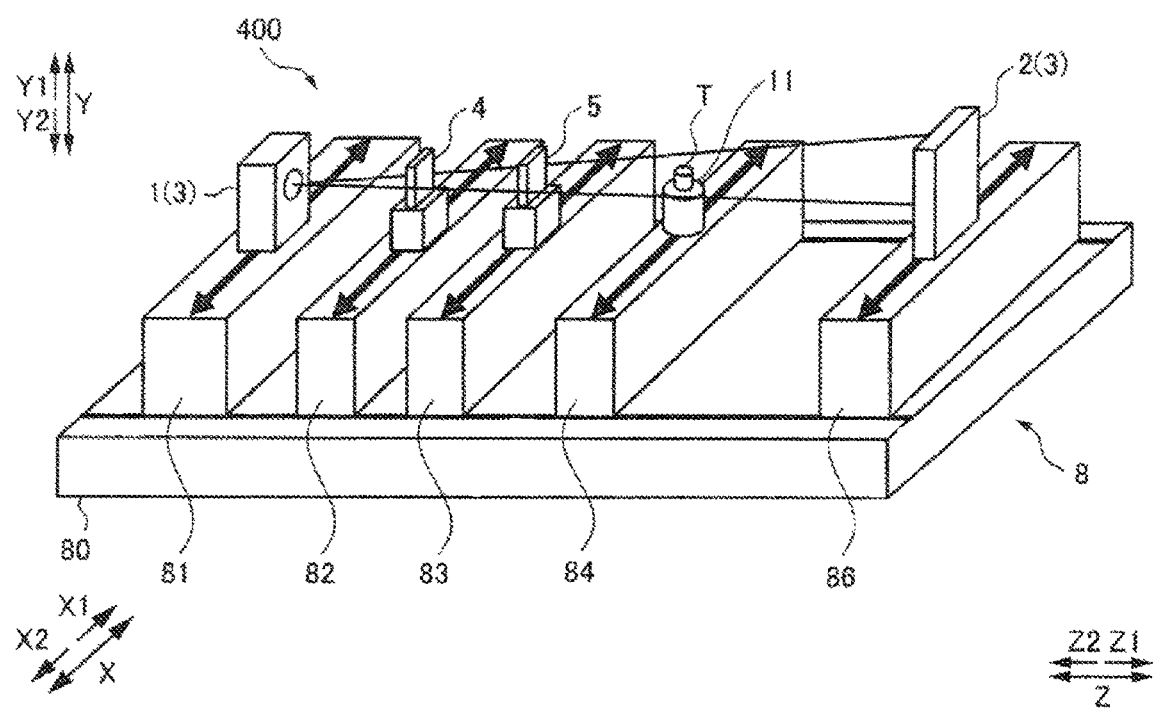
FIG. 11 is a perspective view for explaining detection positions of gratings of the X-ray phase imaging apparatus according to a fourth embodiment of the present invention.
Figure 12:
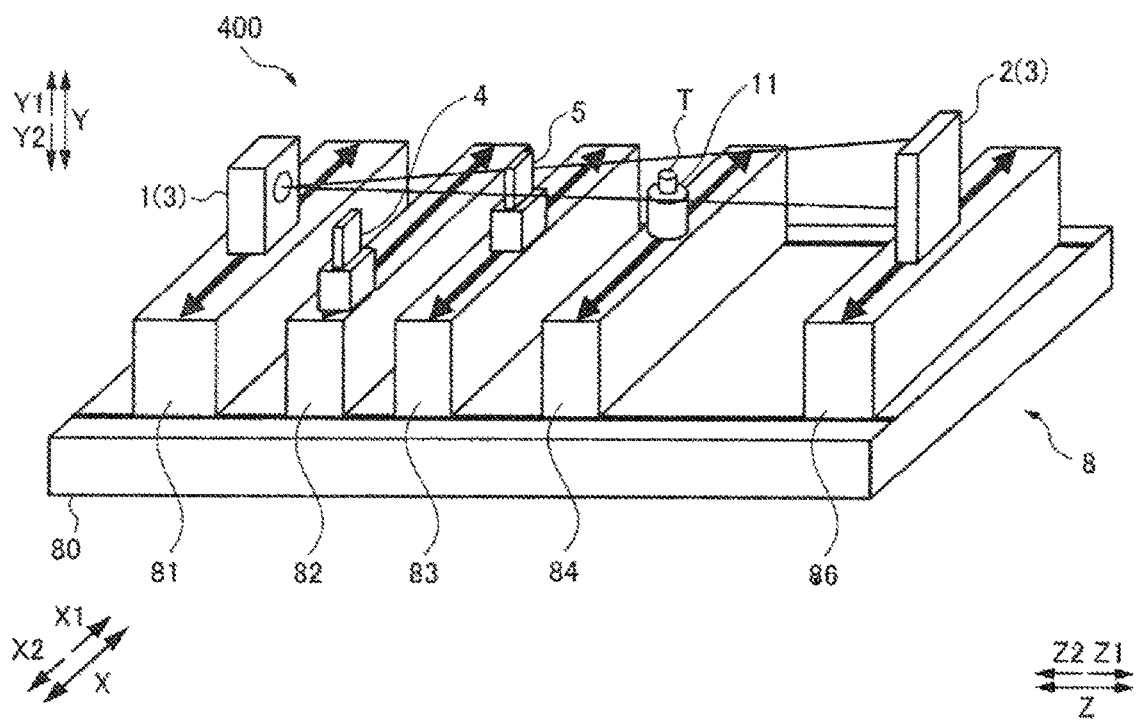
FIG. 12 is a perspective view for explaining a retracted position of a grating of the X-ray phase imaging apparatus according to the fourth embodiment of the present invention.

As shown in FIGS. 11 and 12, in the fourth embodiment, the one or more gratings include two gratings, i.e., a multi-slit 4 for enhancing the coherence of the X-ray irradiated from the X-ray source 1 and a phase grating 5 for forming a self-image 50 by being irradiated by the X-ray passed through the multi-slit 4. Further, the position switching mechanism 8 includes a Z-direction moving mechanism 80, an X-ray source mounting portion 81, a multi-slit mounting portion 82, a phase grating mounting portion 83, an object mounting portion 84, and an image signal detector mounting portion 86.

Further, in the fourth embodiment, since it is configured such that no absorption grating 6 is arranged, in the same manner as in the third embodiment, as the image signal detector 2, a detector 21 having a small pixel pitch is used.

The position switching mechanism 8 is configured to switch at least either the multi-slit 4 or the phase grating 5 between the retracted position and the detection position. That is, the position switching mechanism 8 is configured to move at least either the multi-slit 4 or the phase grating 5 in the X-direction to switch between the retracted position and the detection position.

In the example shown in FIG. 12, it is configured such that the multi-slit 4 is moved in the X2-direction to switch between the retracted position and the detection position. It should be noted that the position switching mechanism 8 may be configured to move the phase grating 5 in the X2-direction. It also may be configured such that the position switching mechanism 8 moves both the multi-slit 4 and the phase grating 5 in the X2-direction.

In the fourth embodiment, the following image can be acquired by changing the focal diameter of the X-ray source 1 in conjunction with the movement of the one or more gratings. That is, by decreasing the focal diameter of the X-ray source 1, arranging the multi-slit 4 in the retracted position and arranging the phase grating 5 in the detection position, a high resolution X-ray phase contrast image can be acquired.

Further, by increasing the focal diameter of the X-ray source 1 and arranging all of the gratings in the detection positions, a low resolution X-ray phase contrast image can be acquired. In addition, by decreasing the focal diameter of the X-ray source 1 and arranging all of the phase gratings in the retracted positions, a high resolution absorption image can be obtained. Further, by increasing the focal diameter of the X-ray source 1 and arranging the multi-slit 4 and/or the phase grating 5 in the retracted position, a low resolution absorption image can be obtained.

Effects of Fourth Embodiment

In the fourth embodiment, the following effects can be obtained.

In the fourth embodiment, as described above, the one or more gratings include two gratings, i.e., a multi-slit 4 for enhancing the coherence of the X-ray irradiated from the X-ray source 1 and a phase grating 5 for forming a self-image 50 by being irradiated by the X-ray passed through the multi-slit 4, and the position switching mechanism 8 is configured to switch at least either the multi-slit 4 or the phase grating 5 between the retracted position and the detection position.

With this, by reducing the focal diameter of the X-ray source 1 and arranging the multi-slit 4 in the retracted position, a high resolution X-ray phase contrast image can be easily acquired. Further, by increasing the focal diameter of the X-ray source 1 and arranging the multi-slit 4 in the detection position, it becomes possible to increase the dose of the X-ray, which in turn can shorten the acquisition time of the X-ray phase contrast image.

The other effects of the fourth embodiment are the same as those of the first embodiment.

Modified Embodiments

It should be understood that the embodiments disclosed here are examples in all respects and are not restrictive. The scope of the present invention is described by claims rather than the descriptions of the embodiments described above, and includes all changes (modifications) within the meaning of equivalent and the scope of claims.

Figure 13:
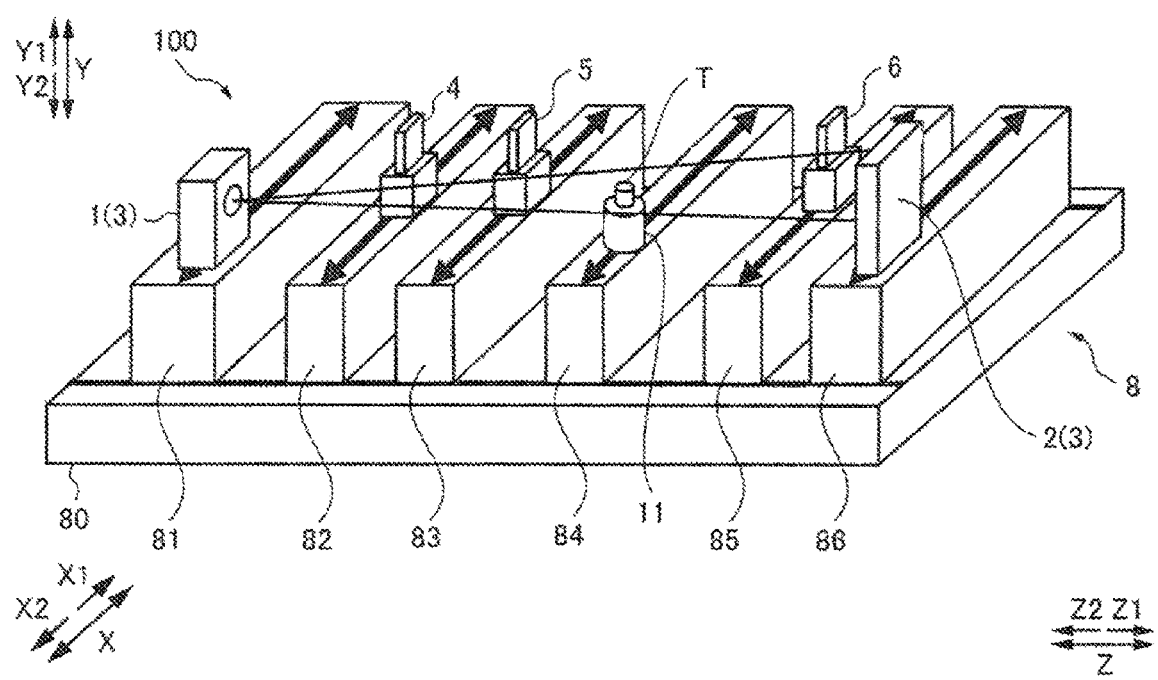
FIG. 13 is a perspective view for explaining retracted positions of gratings of the X-ray phase imaging apparatus according to a first modification of the first embodiment of the present invention.

For example, in the aforementioned first embodiment, the configuration in which the multi-slit 4 is moved to the retracted position is shown, but the present invention is not limited to this. For example, as shown in FIG. 13, it may be configured to move the X-ray source 1, the object T, and the image signal detector 2 to the retracted positions.

In the first embodiment, the example in which the multi-slit 4 and the absorption grating 6 are moved to switch between the retracted position and the detection position is described, but the present invention is not limited to this.

Figure 14:
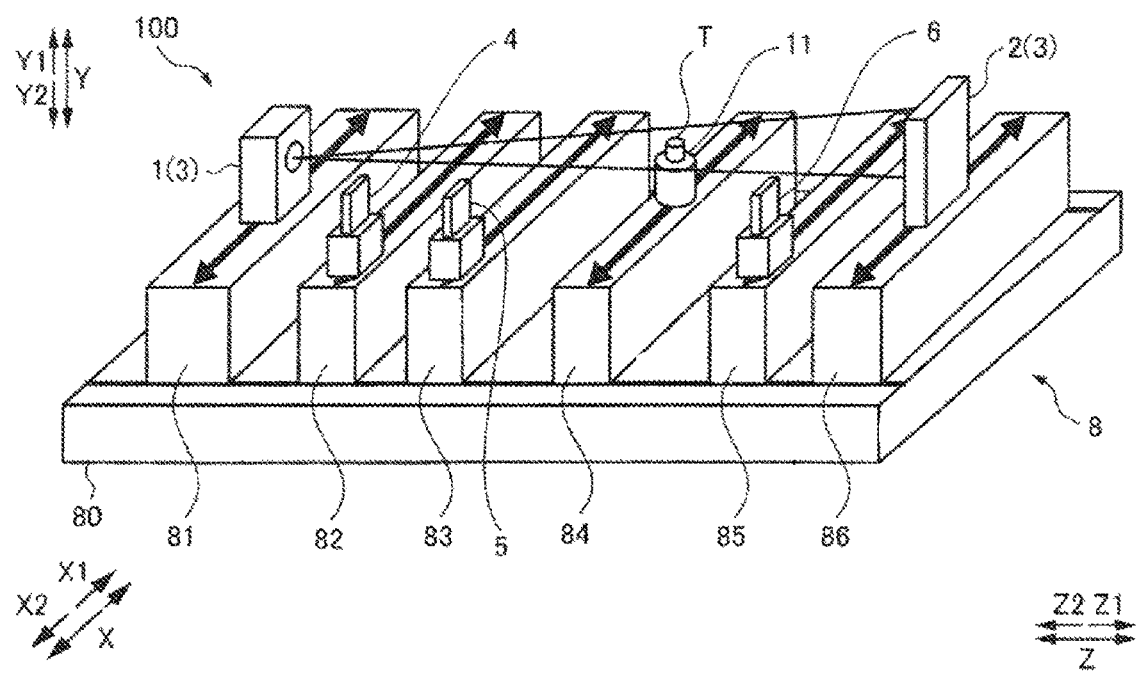
FIG. 14 is a perspective view for explaining retracted positions of gratings of the X-ray phase imaging apparatus according to a second modification of the first embodiment of the present invention.

For example, as shown in FIG. 14, the position switching mechanism 8 may be configured to switch all of the phase gratings between the retracted position and the detection position. With this configuration, at the time of acquiring an absorption image, all of the gratings can be arranged outside the detection range on the detection surface of the image signal detector 2. As a result, the occurrence of an artifact due to one or more gratings arranged within the detection range on the detection surface of the image signal detector 2 can be further suppressed. In addition, since no gratings are arranged within the detection range on the detection surface of the image signal detector 2, it becomes possible to suppress the X-ray attenuation due to gratings, which in turn can shorten the image capturing time.

In the first embodiment, the example in which the X-ray phase imaging apparatus 100 is configured to perform CT image capturing by relatively rotating the object T in the rotational direction about the central axis of the Y-direction is described, but the present invention is not limited to this. For example, it may be configured to perform CT image capturing by relatively rotating the image signal generation system 3 and one or more gratings in the rotational direction about the central axis of the Y-axis direction.

It also may be configured to provide the image signal generation system 3 and one or more gratings in the rotational direction about the central axis of the Y-axis direction and perform CT image capturing.

Figure 17:
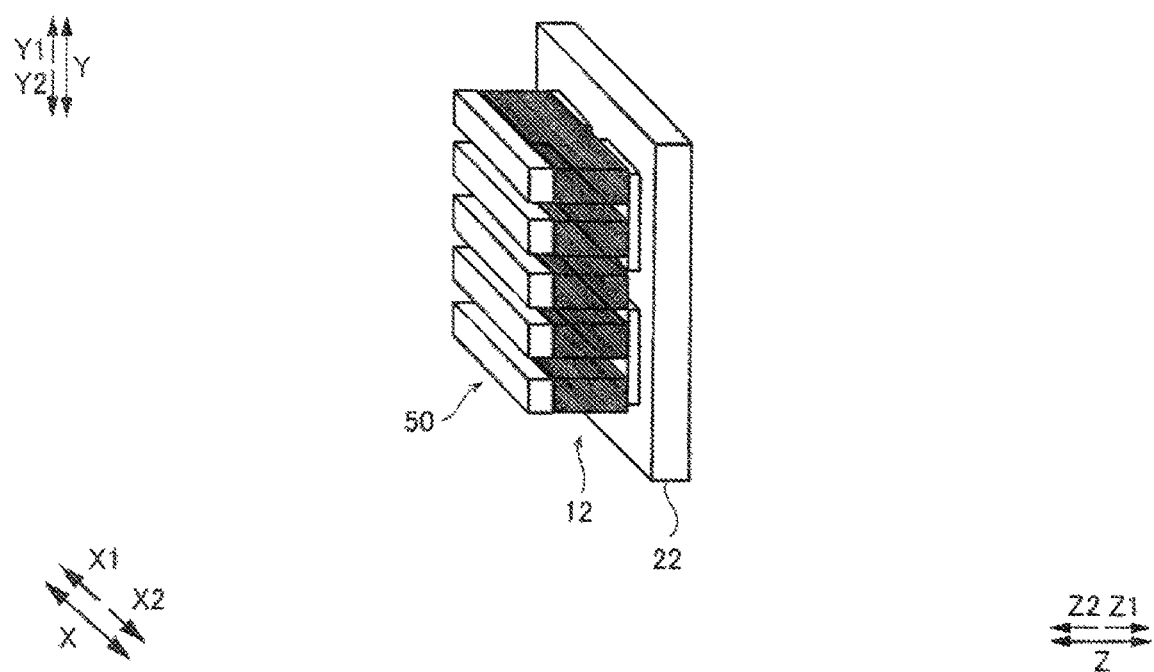
FIG. 17 is a perspective view for explaining the image signal detector of the X-ray phase imaging apparatus according to a fourth modification of the first embodiment of the present invention.

Further, in the first embodiment, the absorption grating 6 is used to form the interference fringe with the self-image 50 of the phase grating 5, but the present invention is not limited thereto. For example, as shown in FIG. 17, it may be configured such that a scintillator 12 configured to detect an X-ray to generate fluorescence and formed in a grating shape is arranged on the detection surface of the detector 22 for detecting light so that the X-ray phase contrast image is obtained by causing interference with the self-image 50 of the phase grating 5.

In the aforementioned second embodiment, as the image signal detector 2, the example in which the detector 2 having a pixel pitch smaller than the period p1 of the self-image 50 of the phase grating 5 is used, but the present invention is not limited to this. For example, as the image signal detector 2, the detector 21 used in the third example may be used. This makes it possible to detect the self-image 50 of the phase grating 5 even in cases where the absorption grating 6 is arranged in the retracted position. Therefore, by increasing the focal diameter of the X-ray source 1 and arranging the absorption grating 6 in the retracted position, a low resolution phase contrast image can be acquired.

In cases where the detector 21 is used as the image signal detector 2, a self-image 50 of the phase grating 5 is formed by decreasing the focal diameter of the X-ray source 1 and arranging the phase grating 5 in the detection position. Therefore, in order to acquire a high resolution absorption image, the focal diameter of the X-ray source 1 is reduced and the phase grating 5 is arranged in the retracted position, and the absorption grating 6 is arranged in the detection position, or the phase grating 5 and the absorption grating 6 are arranged in the retracted positions.

Further, in the first to fourth embodiments, the example in which the focal diameter of the X-ray source 1 is changed by changing the focus control of the X-ray source 1 is shown, but the present invention is not limited to this. For example, it may be configured to change the focal diameter by changing the X-ray source 1 to another X-ray source different in focal diameter.

In the first to fourth embodiments, the example in which the position switching mechanism 8 moves one or more gratings in the X2-direction to switch between the retracted position and the detection position. However, the present invention is not limited to this.

For example, it may be configured such that the position switching mechanism 8 moves one or more phase gratings in the X1-direction to switch between the retracted position and the detection position. Further, it also may be configured to switch between the retracted position and the detection position by combining the X1-direction and the X2-direction instead of either the X1-direction or the X2-direction.

Figure 15:
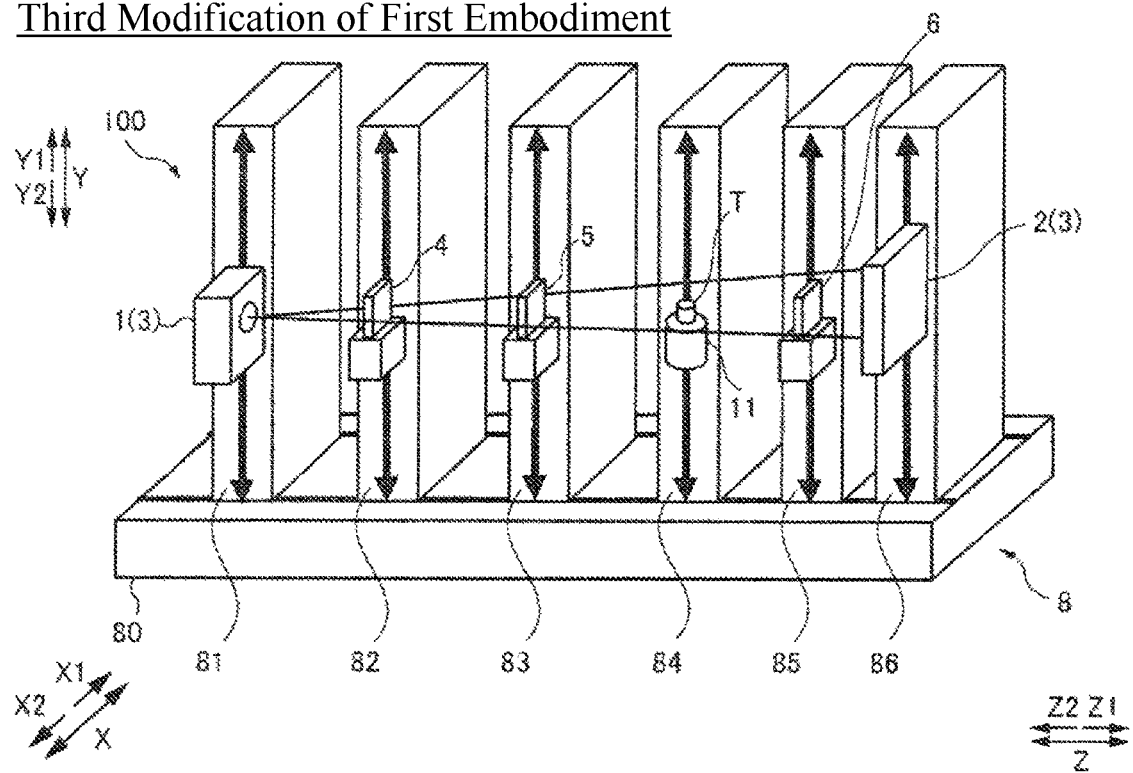
FIG. 15 is a perspective view for explaining detection positions of gratings of the X-ray phase imaging apparatus according to a first modification of the first embodiment of the present invention.
Figure 16:
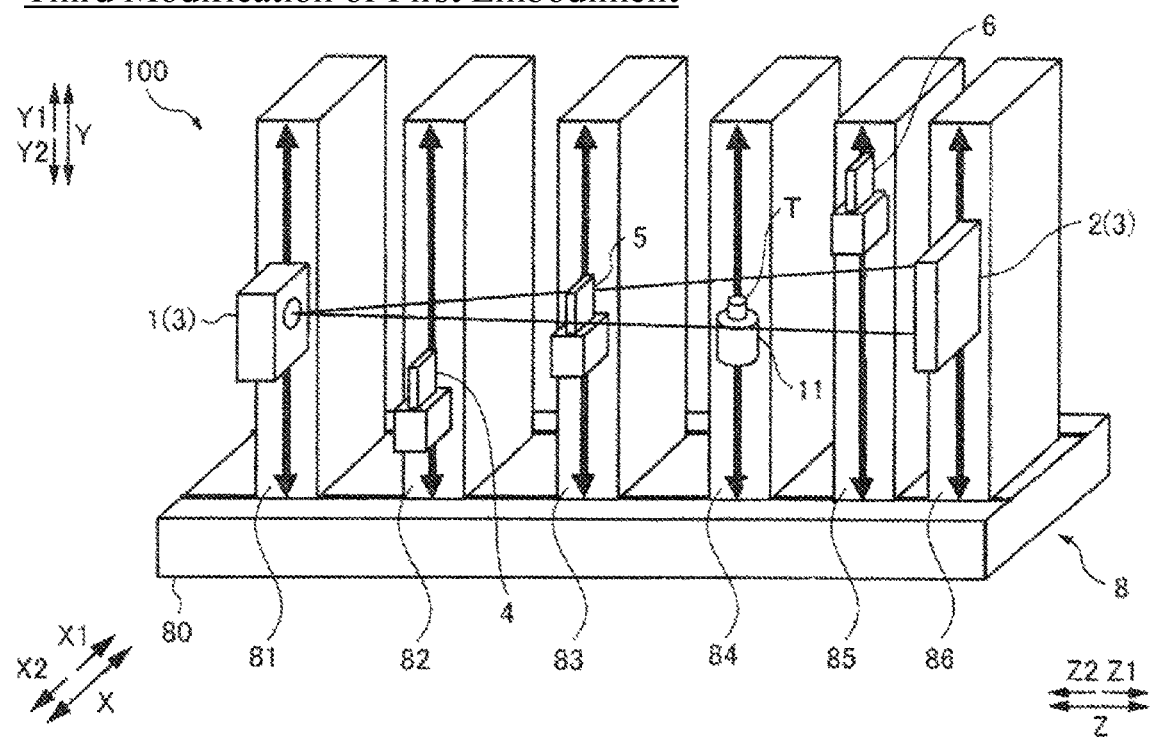
FIG. 16 is a perspective view for explaining retracted positions of gratings of the X-ray phase imaging apparatus according to a third modification of the first embodiment of the present invention.

Further, in the first to fourth embodiments, an example in which the position switching mechanism 8 moves one or more gratings in the X-direction to switch between the retracted position and the detection position. However, the present invention is not limited to this. For example, as shown in FIGS. 15 and 16, it may be configured such that the position switching mechanism 8 moves one or more gratings in the Y1-direction and/or Y2-direction to switch the relative position of the one or more gratings between the retracted position and the detection position.

Further, in the first to fourth embodiments, the example in which an interferometer using the phase grating 5 as a grating for forming the self-image 50 is shown, but the present invention is not limited to this. For example, the X-ray phase imaging apparatus 100 may be configured by a non-interferometer by using an absorption type grating instead of the phase grating 5.

In the first to fourth embodiments, the configuration in which the position switching mechanism 8 linearly moves either one of the gratings in the X-direction or in the Y-direction to switch between the retracted position and the detection position, but the present invention is not limited to this.

For example, the position switching mechanism 8 may be configured to rotate either one of the gratings about the edge to switch between the retracted position and the detection position. However, in cases where the grating is rotated in order to switch between the retracted position and the detection position, there is a high possibility that grating misalignment occurs. Therefore, switching between the retracted position and the detection position is preferably performed by linearly moving the grating.

In the first to fourth embodiments, the example in which the position switching mechanism 8 moves the grating by a single moving mechanism, but the present invention is not limited to this. For example, a single moving mechanism may move multiple gratings. Also, a single moving mechanism may move the X-ray source 1 and gratings. Further, a single moving mechanism may move the image signal detector 2 and gratings.

In addition, in the aforementioned first to fourth embodiments, the example in which a moving mechanism for moving the grating that does not move in the X-direction (Y-direction) in the X-direction (Y-direction) is also provided for switching between the retracted position and the detection position, but the present invention is not limited to this. For example, a grating that does not move in the X-direction (Y-direction) may not have a moving mechanism for moving in the X-direction (Y-direction). This makes it possible to simplify the device configuration.

The invention claimed is:

1. An X-ray phase imaging apparatus comprising:
   an image signal generation system including an X-ray source and an image signal detector for detecting an image signal based on an X-ray irradiated from the X-ray source;
   one or more gratings arranged between the X-ray source and the image signal detector;
   a position switching mechanism configured to relatively move at least either the image signal generation system or the one or more gratings to switch a relative position of the one or more gratings between a retracted position which is an outside of a detection range on a detection surface of the image signal detector and a detection position which is an inside of the detection range on the detection surface of the image signal detector; and
   a focal diameter changing unit configured to change a focal diameter of the X-ray source itself by changing a focus control of the X-ray source, in conjunction with switching of the relative position of the one or more gratings.

2. The X-ray phase imaging apparatus as recited in claim 1, wherein
   the one or more gratings include two gratings, the two gratings including a self-image forming grating for forming a self-image by being irradiated by the X-ray from the X-ray source and an interference fringe forming grating for forming an interference fringe with the self-image of the self-image forming grating by being irradiated by the X-ray passed through the self-image forming grating, and
   the position switching mechanism switches at least either the self-image forming grating or the interference fringe forming grating between the retracted position and the detection position.

3. The X-ray phase imaging apparatus as recited in claim 1, wherein
   the one or more gratings include three gratings, the three gratings including a coherence enhancing grating for enhancing coherence of the X-ray irradiated from the X-ray source, a self-image forming grating for forming a self-image by being irradiated by the X-ray passed through the coherence enhancing grating, and an interference fringe forming grating for forming an interference fringe with the self-image of the self-image forming grating by being irradiated by the X-ray passed through the self-image forming grating, and
   the position switching mechanism switches at least either the coherence enhancing grating or the interference fringe forming grating between the retracted position and the detection position.

4. The X-ray phase imaging apparatus as recited in claim 1, wherein
   the one or more gratings include one grating which is a self-image forming grating for generating a self-image by being irradiated by the X-ray from the X-ray source, and
   the position switching mechanism switches the self-image forming grating between the retracted position and the detection position.

5. The X-ray phase imaging apparatus as recited in claim 1, wherein
   the one or more gratings include two gratings, the two gratings including a coherence enhancing grating for increasing coherence of the X-ray irradiated from the X-ray source and a self-image forming grating for forming the self-image by being irradiated by the X-ray passed through the coherence enhancing grating, and the position switching mechanism switches at least either the coherence enhancing grating or the self-image forming grating between the retracted position and the detection position.

6. The X-ray phase imaging apparatus as recited in claim 1, wherein a plurality of gratings is provided, and the position switching mechanism switches all of the plurality of gratings between the retracted position and the detection position.

7. The X-ray phase imaging apparatus as recited in claim 1, wherein the position switching mechanism moves at least either the image signal generation system or the one or more gratings in a horizontal direction orthogonal to an optical axis direction of the X-ray or a vertical direction to switch the relative position of the one or more gratings between the retracted position and the detection position.

8. The X-ray phase imaging apparatus as recited in claim 1, further comprising a moving mechanism for changing a distance between the X-ray source and the image signal detector in conjunction with switching of the relative position of the one or more gratings.

9. The X-ray phase imaging apparatus as recited in claim 1, further comprising a rotation mechanism for relatively rotating an object and either the image signal generation system or the one or more gratings in a rotational direction about a central axis of a vertical direction orthogonal to an optical axis direction of the X-ray.

* * * * *